(12) United States Patent
Lubisch et al.

(10) Patent No.: US 6,436,949 B1
(45) Date of Patent: Aug. 20, 2002

(54) HETEROCYCLICALLY SUBSTITUTED BENZAMIDES AND THEIR USE

(75) Inventors: Wilfried Lubisch, Mannheim; Achim Möller, Grüstadt; Hans-Jörg Treiber, Brühll, all of (DE)

(73) Assignee: Abbott Laboratories, Abbott Park, IL (US)

( * ) Notice: Subject to any disclaimer, the term of this patent is extended or adjusted under 35 U.S.C. 154(b) by 5 days.

(21) Appl. No.: 09/666,304

(22) Filed: Sep. 21, 2000

Related U.S. Application Data

(62) Division of application No. 09/308,350, filed as application No. PCT/EP97/06653 on Nov. 28, 1997.

(30) Foreign Application Priority Data

Dec. 9, 1996 (DE) .......................................... 196509975

(51) Int. Cl.$^7$ ...................... A61K 31/40; A61K 31/505; C07D 209/02; C07D 239/70

(52) U.S. Cl. ........................ 514/274; 514/418; 514/257; 514/267; 548/452; 548/465; 548/473; 548/477; 544/249; 544/309

(58) Field of Search ................................ 548/452, 465, 548/473, 477; 514/418, 257, 267, 274; 544/249, 309

(56) References Cited

FOREIGN PATENT DOCUMENTS

| DE | 3717828 | * 12/1988 |
|----|---------|-----------|
| EP | 0 520 336 | 12/1992 |
| WO | 91/09801 | 7/1991 |
| WO | 92/11850 | 7/1992 |
| WO | 9212150 | 7/1992 |
| WO | 94/00095 | 1/1994 |
| WO | 95/00535 | 1/1995 |

OTHER PUBLICATIONS

Angelastro et al. alpha–Diketone and alpha–keto ester derivatives of N–protected amino acids and peptides as novel inhibitors of cyctein and serin proteinases, J. Med. Chem. 33, 11–13 (1990).
Angliker et al. Inactivation of calpain by peptidyl fluoromethyl ketones, Ja. Med. Chem. 35(2),216–200 (1992).
Barrett et al. Effect of substrate on Ca$^{2+}$ concentration required for activity of the Ca$^{2+}$ dependent proteinases, Life Sci. 48, 1659–1669 (1991).
Bartus et al. Calpain as a novel target for treating acute neurodegenerative disorders, Neurl. Res. 17, 249–258 (1995).
Burkhart et al. Oxidation of alpha–hydroxy esters to alpha-–keto esters using the Dess–Martin periodinane reagent Tetrahedron lett. 29(28), 3433–3436 (1988).

Derwent Abstract 96–387165/39 (1998) New amide derivs, has calpain inhibitory activity—useful for treating ischhaemic disorders, neuropathy, myodystrophy and cataracts; JP–A 08/183,771 (1994).
Derwent Abstract 96–379278/38 (1998) New cyclo–alkylene amide derivs, having calpain inhibitory activity—used for treating ischhaemic disorders, neuropathy, myodystrophy and cataract; JP–A 08/183,769 (1994).
Derwent Abstract 96–379271/38 (1998) Amide derivs, with calpain inhibitory activity—useful in treatment of e.g. ischhaemia, neuropathy, muscle dysthophy and cataract; JP–A 08/183,759 (1994).
Edelstein et al. The role of cystein protease in hyproxia–induced rat renal proximal tubular injury, Proc. Natl. Acad. Sci. 92, 7662–7666 (1995).
Fehrentz et al. An efficient synthesis of optically active alpha–(t–butoxycarbonylamino)aldehydes from alpha–amino acids, Synthesis Com. 8, 676–678 (1983).
Haberson et al. Inhibitors of Calpain J. Med. Chem. 37(18) 2927–2929 (1994).
Higaki et al. Inhibition of beta–amloid formation identifies proteolytic precursors and subcellular site of catabolism, Neuron 14, 651–659 (1995).
Hong et al. Neuroprotection with a calpain inhibitor in a model fo focal cerebral ischemia, Stroke 25(3), 643–669 (1994).
Li et al. Peptide alpha–keto ester, alpha–keto amide, and alpha keto acid inhibitors of Calpain and other cystein proteases, J. Med. Chem. 36(22), 3472–3480 (1993).
Matsueda et al. Potent affinity labeling peptide inhibitors of calpain, Chem. Lett. 191–194 (1990).
McGowan et al. Inhibition of calpain in intact platelets by the thiol protease inhibitor E–64d, Biochem. Biophys. Res. Comm. 158(2), 432–435 (1989).
Mehdi Cell penetrating inhibitors of calpain, TIBS 16(4), 150–153 (1991).
Mondola et al. Role of a calf thymus preparation in the degradation of native and reductively methylated low density lipoprotein, Int. J. Biochem. 23(9), 819–821 (1991).
Saatman et al. Calpain inhibitor AK95 attenuated motor and cognitive deficits following experimental brain injury in the rat, Proc. Natl. Acad. Sci. 93, 3428–3433 (1996).

(List continued on next page.)

Primary Examiner—Richard L. Raymond
Assistant Examiner—Sudhaker B. Patel
(74) Attorney, Agent, or Firm—Keil & Weinkauf

(57) ABSTRACT

Heterocyclically substituted benzamides of the formula I

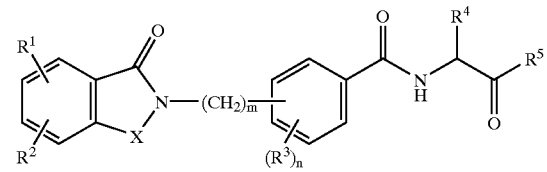

are described, where $R^1, R^2, R^3, R^4, R^5$, X, m and n have the meanings given in the description. The novel compounds are useful for controlling diseases.

21 Claims, No Drawings

OTHER PUBLICATIONS

Shiba et al. Mechanism of growth inhibition of MCF–7 by a cell permeable calpain inhibitor, INt. J. Oncol. 5 Supp. 381 (1994).

Suzuki et al. Calpain: novel family members, activation, and physiological function, Biol. Chem. Hoppe–Seyl–er 376, 523–529 (1995).

Wang et al. Calpain inhibition: an overview of its therapeutic potential, TIPS 15(11), 412–419 (1994).

Watanabe et al. Selective release of a processed fofrm of interleukin 1alpha, Cyotkine 6(6), 597–601 (1994).

Yoshida et al. Calpain is implicated in rat myocardial injury after ischemia of reperfusion, Jap Circ. J. 59(1), 40–48 (1995).

* cited by examiner

HETEROCYCLICALLY SUBSTITUTED BENZAMIDES AND THEIR USE

This is a Divisional Application of Application Ser. No. 09/308,350, filed on May 19, 1999, which is a National Stage Application under 35 U.S.C. 371, based on International Application No. PCT/EP97/06,653, filed Nov. 28, 1997.

The present invention relates to novel heterocyclically substituted benzamides and their use in the control of diseases.

Calpains are intracellular, proteolytic enzymes from the cysteine protease group and are found in many cells. Calpains are activated by an elevated concentration of calcium, with a distinction being made between calpain I or μ-calpain, which is activated by μmolar concentrations of calcium ions, and calpain II or m-calpain, which is activated by mmolar concentrations of calcium ions (P. Johnson, Int.J.Biochem. 1990, 22(8), 811–22). Nowadays, the existence of other calpain isoenzymes is also postulated (K. Suzuki et al., Biol.Chem. Hoppe-Seyler, 1995, 376(9), 523–9).

Calpains are presumed to play an important role in various physiological processes including the cleavage of regulatory proteins such as protein kinase C, cytoskeletal proteins such as MAP 2 and spectrin, and muscle proteins, protein degradation in rheumatoid arthritis, proteins associated with the activation of platelets, neuropeptide metabolism, proteins in mitosis and others which are listed in M. J. Barrett et al., Life Sci. 1991, 48, 1659–69 and K. K. Wang et al., Trends in Pharmacol.Sci., 1994, 15, 412–9.

Elevated levels of calpain have been measured in various pathophysiological processes, for example: ischemias of the heart (eg. cardiac infarction), of the kidney or of the central nervous system (eg. stroke), inflammations, muscular dystrophies, cataracts of the eyes, injuries to the central nervous system (eg. trauma), Alzheimer's disease, etc. (see K. K. Wang, above). These diseases have a presumed association with elevated and persistent intracellular calcium levels, which cause calcium-dependent processes to be overactivated and no longer subject to physiological control. In a corresponding manner, overactivation of calpains can also trigger pathophysiological processes.

For this reason, it was postulated that inhibitors of the calpain enzymes might be of value for treating these diseases. This has been confirmed by a variety of investigations. For example, Seung-Chyul Hong et al., Stroke 1994, 25(3), 663–9 and R. T. Bartus et al., Neurological Res. 1995, 17, 249–58 have demonstrated that calpain inhibitors have a neuroprotective effect in acute neurodegenerative disturbances or ischemias, as occur following cerebral stroke. Calpain inhibitors improved recovery from the memory performance deficits and neuromotor disturbances which occurred following experimental brain traumas (K. E. Saatman et al. Proc.Natl.Acad.Sci. USA, 1996, 93,3428–3433). C. L. Edelstein et al., Proc.Natl.Acad.Sci. USA, 1995, 92, 7662–6 found that calpain inhibitors have a protective effect on hypoxia-damaged kidneys. Yoshida, Ken Ischi et al., Jap.Circ.J. 1995, 59(1), 40–8, were able to demonstrate that calpain inhibitors exerted beneficial effects following cardiac damage caused by ischemia or reperfusion. Since calpain inhibitors inhibit the release of the β-AP4 protein, a potential use was proposed for them as therapeutic agents in Alzheimer's disease (J. Higaki et al., Neuron, 1995, 14, 651–59). Calpain inhibitors also inhibited the release of interleukin-1α (N. Watanabe et al., Cytokine 1994, 6(6), 597–601). In addition, it was found that calpain inhibitors have cytotoxic effects on tumor cells (E. Shiba et al. 20th Meeting Int.Ass.Breast Cancer Res., Sendai Jp, Sept. 25–28. 1994, Int.J.Oncol. 5(Suppl.), 1994, 381).

Other possible uses of calpain inhibitors are listed in K. K. Wang, Trends in Pharmacol.Sci., 1994, 15, 412–8.

Calpain inhibitors have been described in the literature. However, these are predominantly either irreversible inhibitors or peptide inhibitors. As a rule, irreversible inhibitors are alkylating substances and suffer from the disadvantage that they react nonselectively in the organism or are unstable. Thus, these inhibitors often have undesirable side effects, such as toxicity, and are therefore of limited use or are unusable. Examples of the irreversible inhibitors are E 64 epoxides (E. B. McGowan et al., Biochem.Biophys.Res-.Commun. 1989, 158, 432–5), α-haloketones (H. Angliker et al., J.Med.Chem. 1992, 35, 216–20) and disulfides (R. Matsueda et al., Chem.Lett. 1990, 191–194).

Many known reversible inhibitors of cysteine proteases such as calpain are peptide aldehydes, in particular dipeptide or tripeptide aldehydes such as Z-Val-Phe-H (MDL 28170) (S. Mehdi, Trends in Biol.Sci. 1991, 16, 150–3) and the compounds from EP 520336.

Peptide ketone derivatives have also been found to be inhibitors of cysteine proteases, in particular calpain. However, only those ketones in which, on the one hand, α-terminal leaving groups cause an irreversible inhibition and, on the other, a carboxylic acid derivative activates the keto group, have been found to be effective inhibitors (see M. R. Angelastro et al., J.Med.Chem. 1990,33, 11–13; WO 92/11850; WO 92,12140; Wo 94/00095 and WO 95/00535). However, only peptide derivatives of these ketoamides and keto esters have so far been reported to be active (Zhao Zhao Li et al., J.Med.Chem. 1993, 36, 3472–80; S. L. Harbenson et al., J.Med.Chem. 1994, 37, 2918–29 and see M. R. Angelastro et al. above).

Ketobenzamides are known in the literature. For example, the keto ester PhCO—Abu—COOCH$_2$CH$_3$ has been described in WO 91/09801, WO 94/00095 and 92/11850. However, M. R. Angelastro et al., in J.Med.Chem. 1990,33, 11–13 found the analogous phenyl derivative Ph—CONH—CH(CH$_2$Ph)—CO—COCOOCH$_3$ to be only a weak inhibitor of calpain. This derivative is also described in J. P. Burkhardt, Tetrahedron Lett., 1988, 3433–36. However, the importance of the substituted benzamides has so far never been investigated.

JP 8183759, JP 8183769, JP 8183771 and EP 520336 describe aldehydes which were derived from dipeptides, with saturated carbocyclic rings, for example cyclohexanes, or saturated heterocyclic rings, for example piperidines, being incorporated into these peptide inhibitors in place of an amino acid, thereby giving rise to novel aldehydes which were calpain inhibitors.

Substituted, non-peptide, heterocyclically substituted benzamide derivatives having an improved effect have now been found.

The present invention relates to heterocyclically substituted benzamides of the formula I

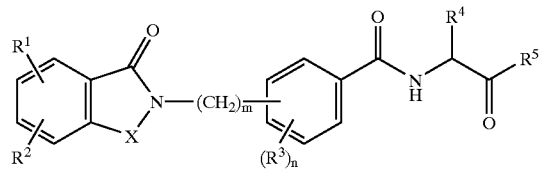

and their tautomeric and isomeric forms, and also, where appropriate, physiologically tolerated salts, where the variables have the following meanings:

$R^1$ is hydrogen, $C_1-C_6$-alkyl, $O-C_1-C_6$-alkyl, OH, Cl, F, Br, I, $CF_3$, $NO_2$, $NH_2$, CN, COOH, $COO-C_1-C_4$-alkyl, $-NHCO-C_1-C_4$-alkyl, $-NHCO$-phenyl, $-CONHR^8$, $NHSO_2-C_1-C_4$-alkyl, $-NHSO_2$-phenyl, $-SO_2-C_1-C_4$-alkyl or $-SO_2$-phenyl, $R^2$ is hydrogen, $C_1-C_6$-alkyl, $O-C_1-C_6$-alkyl, OH, Cl, F, Br, I, $CF_3$, $NO_2$, $NH_2$, CN, COOH, $COO-C_1-C_4$-alkyl, $-NHCO-C_1-C_4$-alkyl, $-NHCO$-phenyl, $-CONHR^8$, $NHSO_2-C_1-C_4$-alkyl, $-NHSO_2$-phenyl, $-SO_2-C_1-C_4$-alkyl or $-SO_2$-phenyl or $R^1$ and $R^2$ are, together, a chain $-CH=CH-CH=CH-$, which can additionally carry one or two substituents $R^6$, $R^3$ is hydrogen, chlorine, bromine, fluorine, $C_1-C_6$-alkyl, phenyl, $NHCO-C_1-C_4$-alkyl, $NO_2$ or $NH_2$, $R^4$ is $C_1-C_6$-alkyl, which can additionally carry a phenyl cyclopropyl, cyclobutyl, cyclopentyl, cyclohexyl, cycloheptyl, indolyl, pyridyl or naphthyl ring which, for its part, is substituted by one or two radicals $R^7$, with $R^7$ being hydrogen, $C_1-C_4$-alkyl, $-O-C_1-C_4$-alkyl, OH, Cl, F, Br, I, $CF_3$, $NO_2$, $NH_2$, CN, COOH, $COO-C_1-C_4$-alkyl, $-CONHR^8$, $-NHCO-C_1-C_4$-alkyl, $-NHCO$-phenyl, $-NHSO_2-C_1-C_4$-alkyl, $-NHSO_2$-phenyl, $-SO_2-C_1-C_4$-alkyl or $-SO_2$-phenyl, $R^5$ is hydrogen, $-CO-OR^8$, $-CO-NR^9R^{10}$,

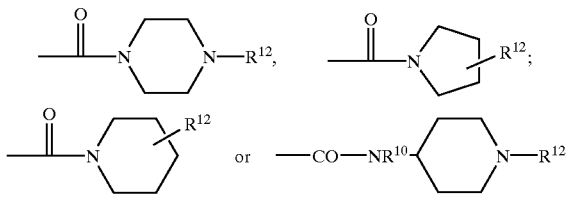

$R^6$ is hydrogen, $C_1-C_6$-alkyl, $-O-C_1-C_6$-alkyl, OH, Cl, F, Br, I, $CF_3$, $NO_2$, $NH_2$, CN, COOH, $COO-C_1-C_4$-alkyl, $R^8$ is hydrogen or $C_1-C_6$-alkyl, $R^9$ is hydrogen or $C_1-C_6$-alkyl which can additionally be substituted by a phenyl ring which can additionally carry a radical $R^{11}$ and can be substituted by

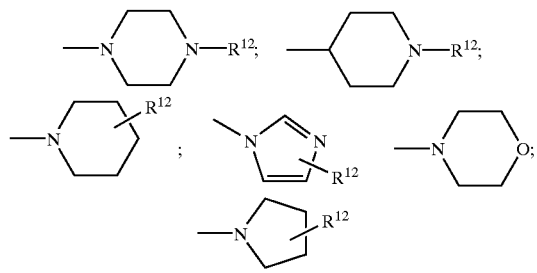

$R^{10}$ is hydrogen or $C_1-C_6$-alkyl, $R^{11}$ is hydrogen, $C_1-C_6$-alkyl, $-O-C_1-C_6$-alkyl, OH, Cl, F, Br, I, $CF_3$, $NO_2$, $NH_2$, CN, COOH or $COO-C_1-C_4$-alkyl, $R^{12}$ is hydrogen or a $C_{0-4}$-alkyl chain which can be substituted by a phenyl ring which can itself additionally carry one or two radicals $R^{11}$, X is $-NH-CO-$, $-N=CH-$, $-CH_2-CH_2-$, $-CH=CH-$, $-SO_2-$, $-CH_2-$, $-CO-$ and $-CH_2-CO-$, n is the number 0, 1 or 2, and m is the number 0, 1 and 2.

Preference is given to heterocyclically substituted benzamides of the formula I as claimed in claim 1, where $R^5$ is hydrogen, and $R^1$, $R^2$, $R^3$, $R^4$, x m and n have the abovementioned meanings.

Preference is furthermore given to heterocyclically substituted benzamides of the formula I, as claimed in claim 1, where $R^5$ is $-CO-NR^9R^{10}$, and $R^1$, $R^2$, $R^3$, $R^4$, x, m and n have the abovementioned meanings.

Finally, preference is also given to heterocyclically substituted benzamides of the formula I as claimed in claim 1, where $R^5$ is $-CO-OR^8$, and $R^1$, $R^2$, $R^3$, $R^4$, x, m and n have the abovementioned meanings.

The compounds of formula I can be employed as racemates or as enantiomerically pure compounds or as diastereomers. If enantiomerically pure compounds are desired, these can be obtained, for example, by carrying out a conventional racemate resolution with the compounds of the formula I or their intermediates using a suitable optically active base or acid. On the other hand, the enantiomeric compounds can also be prepared by employing commercially available compounds, for example optically active amino acids such as phenylalanine, tryptophan and tyrosine.

The present invention also relates to the compounds which are mesomeric and tautomeric in relation to the compounds of the formula I, for example those compounds in which the keto group of the formula I is present as an enol tautomer.

Some of the novel compounds I can contain a basic or acidic group. In these cases, the compounds I can be present in the form of their physiologically tolerated salts, which can be obtained by reacting the compounds I with a suitable acid or base.

Suitable acids for forming salts with novel compounds I which contain a basic group can, for example, be hydrochloric acid, citric acid, tartaric acid, lactic acid, phosphoric acid, methanesulfonic acid, acetic acid, formic acid, maleic acid, fumaric acid, malic acid, succinic acid, malonic acid and sulfuric acid. Suitable bases are, for example, potassium hydroxide, sodium hydroxide, lithium hydroxide, triethylamine, α,α,α-tris(hydroxymethyl)methylamine and other amines.

The ketobenzamides I according to the invention can be prepared in a variety of ways, which have been outlined in synthesis schemes 1, 2 and 3.

The carboxylic esters II are converted into the acids III using acids or bases such as lithium hydroxide, sodium hydroxide or potassium hydroxide in aqueous medium or in mixtures composed of water and organic solvents such as alcohols or tetrahydrofuran at room temperature or elevated temperatures, such as 25–100° C. The acids III are linked to an α-amino acid derivative using customary conditions which are listed, for example, in Houben-Weyl, Methoden der organischen Chemie [Methods of Organic Chemistry], 4th Edtn., E5, Ch. V, and C. R. Larock, Comprehensive Organic Transformations, VCH Publisher, 1989, Ch.9.

The carboxylic acids III are converted into "activated" acid derivatives R'—COOL, with L being a leaving group such as Cl, imidazole and N-hydroxybenzotriazole, and then converted into the derivative IV by reaction with an amino acid derivative $H_2N-CH(R4)-COOR$. This reaction is carried out in anhydrous, inert solvents such as methylene chloride, tetrahydrofuran and dimethylformamide at from −20 to +25° C.

Scheme 1

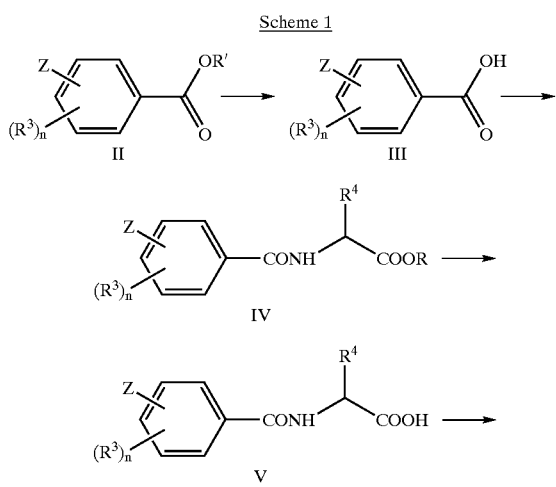

a reaction which is analogous to the Dakin-West reaction, using a method of Zhao Zhao Li et al., J.Med.Chem., 1993, 36, 3472–80. In this reaction, a carboxylic acid, such as V, is reacted, at elevated temperature (50–100° C.) in solvents, such as tetrahydrofuran, with an oxalyl chloride monoester and the resulting product is then reacted with bases, such as sodium ethoxide, in ethanol at 25–80° C. to give the ketoester I' according to the invention. The ketoesters I' can, as described above, be hydrolyzed to give the ketocarboxylic acids according to the invention.

Conversion into the ketobenzamides I' is likewise effected using a method which is similar to that of Zhao Zhao Li et al. (see above). The keto group in I' is protected by adding 1,2-ethanedithiol while employing Lewis acid catalysis, for example using boron trifluoride etherate, in inert solvents, such as methylene chloride, at room temperature, resulting in a dithiane. These derivatives are reacted with amines $R^3$-H in polar solvents, such as alcohols, at 0–80° C., thereby giving rise to the ketoamides I ($R^4 = NR^7R^8$).

Scheme 2

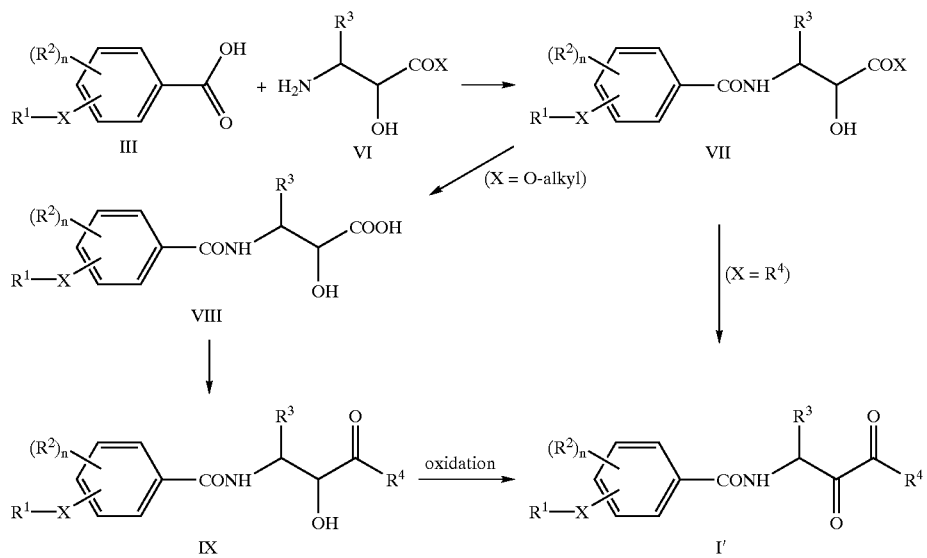

-continued

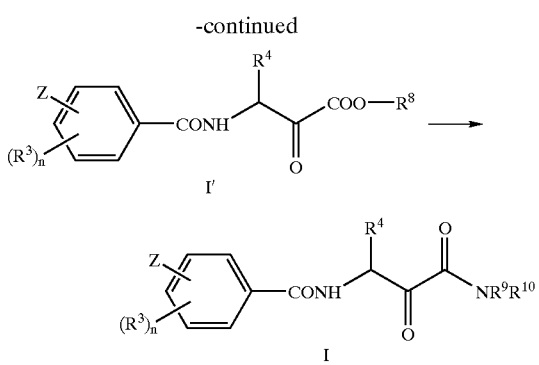

The derivatives IV, which as a rule are esters, are converted into the ketocarboxylic acids V in analogy with the above-described hydrolysis. The ketoesters I' are prepared in An alternative method is depicted in Scheme 2. The ketocarboxylic acids III are reacted with aminohydroxycarboxylic acid derivatives VI (Preparation of VI, see S. L. Harbenson et al., J.Med.Chem. 1994, 37, 2918–29) using customary peptide coupling methods (see Houben-Weyl above), resulting in the amides VII. These alcohol derivatives VII can be oxidized to give the ketocarboxylic acid derivatives I according to the invention. A variety of customary oxidation reactions (see C. R. Larock, Comprehensive Organic Transformations, VCH Publisher, 1989, page 604 f.), such as Swern oxidations and Swern-analogous oxidations, can be used for this purpose. Preference is given to using a dimethyl sulfoxide/pyridine-sulfur trioxide complex in solvents such as methylene chloride or tetrahydrofuran, with or without the addition of dimethyl sulfoxide, at room temperature or at from −50 to 25° C., (T. T. Tidwell, Synthesis 1990, 857–70) or sodium hypochlorite/TEMPO (S. L. Harbenson et al., see above).

The α-hydroxy esters VII (X=O-alkyl) can be hydrolyzed to carboxylic acids VIII using similar methods to those above, preferably, however, using lithium hydroxide in water/tetrahydrofuran mixtures at room temperature. Other esters or amides X are prepared by reacting with alcohols or amines under the previously described coupling conditions. The alcohol derivative IX can also be oxidized to give the ketocarboxylic acid derivative I according to the invention.

The aldehydes according to the invention of the formula I ($R^5$=hydrogen) can be prepared by a method similar to that shown in synthesis scheme 3. Benzoic acid derivatives III are linked to suitable aminoalcohols X to give the corresponding benzamides XI. For this, use is made of customary peptide coupling methods which are described either in C. R. Larock, Comprehensive Organic Transformations, VCH Publisher, 1989, page 972 f. or in Houben-Weyl, Methoden der organischen Chemie [Methods of Organic Chemistry], 4th Edtn., E5, Ch. V. "Activated" acid derivatives of III, in which the acid group COOH is converted into a COL group, are preferably used. L represents a leaving group such as Cl, imidazole and N-hydroxybenzotriazole. This activated acid is then reacted with amines to give the amides XI. The reaction is carried out in anhydrous, inert solvents, such as methylene chloride, tetrahydrofuran and dimethylformamide, at from −20 to +25° C.

Alternatively, the benzoic acid III can be reacted with aminohydroxamic acid derivatives XIII to give benzamides XIII. The reaction is conducted in the same way as when preparing XI. The hydroxamic derivatives XIII can also be obtained from the protected amino acids XII by reacting them with hydroxylamine. The previously described amide preparation methods are then used in this case as well. The protecting group $Y^2$, for example Boc, is eliminated in a customary manner, for example using trifluoroacetic acid in methylene chloride. The benzamide-hydroxamic acids XIV which are obtained in this way can be converted by reduction into the aldehydes I according to the invention. For this, lithium aluminum hydride is used, for example, as the reducing agent, at from −60 to 0° C. and in inert solvents such as tetrahydrofuran or ether.

Benzamide-carboxylic acids or acid derivatives, such as esters or amides XV, which can likewise be converted by reduction into the aldehydes I according to the invention, can also be prepared using methods which are similar to the latter method. These methods are described in R. C. Larock, Comprehensive Organic Transformations, VCH Publisher, 1989, pages 619–26.

Synthesis scheme 3

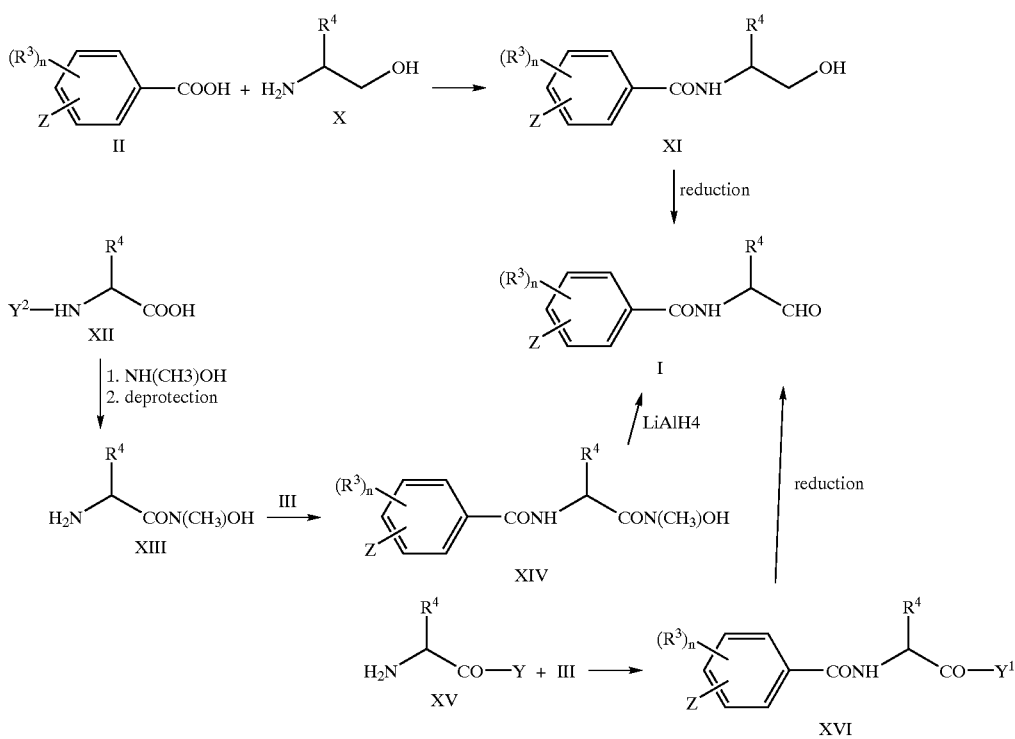

The alcohol derivative XI can be oxidized to give the aldehyde derivative I according to the invention. A variety of customary oxidation reactions (see C. R. Larock, Comprehensive Organic Transformations, VCH Publisher, 1989, page 604 f.), such as Swern oxidations and Swern-analogous oxidations. (T. T. Tidwell, Synthesis, 1990, 857–70), sodium hypochlorite/TEMPO (S. L. Harbenson et al., see above) or Dess-Martin (J.Org.Chem. 1983, 48, 4155) can be used for this purpose. Preference is given to carrying out the reaction in inert aprotic solvents such as dimethylformamide, tetrahydrofuran or methylene chloride and using oxidizing agents such as DMSO/pyridine×$SO_3$ or DMSO/oxalyl chloride at from −50 to +25° C.

The synthesis of the carboxylic esters II and the carboxylic acids III has been described previously in some cases or the esters II and acid III can be prepared in accordance with customary chemical methods.

Thus, the precursors II of the pyrimidiones I (X═—NH—CO—) can be prepared from the corresponding isatoic anhydrides (see C. K. Reddy et al., Ind.J.Chem., 1987, 26B, 882) or directly from the 2-aminobenzoic acid derivatives by reacting with phenyl isocyanates (see: C. M. Gupta et al., Ind.J.Chem. 1968, 6B, 621; Czech. 128, 433(CA 70, 115176)).

The analogous pyrimidones (cf. I and II, X═—NH═CH—) can be obtained by condensing orthoaminobenzamides with formaldehyde equivalents (see B. Denis et al., J.Med.Chem. 1985, 24, 531; H. Suesse et al., J.Pract.Chem. 1984, 326, 1027).

Imides (X=—CO—, or —CH$_2$—CO—) can be synthesized from the corresponding anhydrides of the dicarboxylic acids (see: J. M. Chapman et al., J.Med.Chem. 1983, 26, 237; K. Pinney et al., J.Org.Chem., 1991, 56, 3125; IY.Imai et al., Nippon Kagaku Kaishi 1975, 2954 (CA 84, 105522)). The phthalazinones (X=—CH=N—) can be prepared from phenylhydrazines and ortho-substituted benzoic acid derivatives (see: J. E. Francis et al., Can.J.Chem. 1982, 60, 1214). Lactams (X=—CH$_2$—; —CH$_2$—CH$_2$—) can be obtained from the imides, for example, by reduction (see: J. Brewster et al., J.Org.Chem. 1963, 28, 501; GB 2204579; R. Sato et al., Bull.Chem.Soc.Jpn., 1988, 61, 2238).

The ketobenzamides I according to the invention are inhibitors of cysteine proteases, in particular cysteine proteases such as calpains I and II and cathepsins B and L.

The inhibiting effect of the ketobenzamides I was determined using enzyme tests which are customary in the literature, with the concentration of the inhibitor at which 50% of the enzyme activity is inhibited (=IC$_{50}$) being determined as the measure of efficacy. The K$_i$ value was also determined in some cases. These criteria were used to measure the inhibitory effect of the ketobenzamides I on calpain I, calpain II and cathepsin B.

Cathepsin B Test

Inhibition of cathepsin B was determined by a method which was similar to a method of S. Hasnain et al., J.Biol.Chem. 1993, 268, 235–40.

2 μL of an inhibitor solution, prepared from inhibitor and DMSO (final concentrations: 100 μM bis 0.01 μM) are added to 88 μL of cathepsin B (human liver cathepsin B (Calbiochem) diluted to 5 units in 500 μM buffer). This mixture is preincubated at room temperature (25° C.) for 60 min and the reaction is then starting by adding 10 μL of 10 mM Z-Arg-Arg-pNA (in buffer containing 10% DMSO). The reaction is followed at 405 nm for 30 min in a microtiter plate reader. The IC$_{50}$'s are then determined from the maximum slopes.

Calpain I and II Test

The inhibitory properties of calpain inhibitors are tested in buffer containing 50 mM Tris-HCl, pH 7.5; 0.1 M NaCl; 1 mM dithiotreithol [sic]; 0.11 mM CaCl$_2$, using the fluorogenic calpain substrate Suc-Leu-Tyr-AMC (25 mM dissolved in DMSO, Bachem/Switzerland) (Sasaki et al. J. Biol. Chem. 1984, Vol. 259, 12489–12494). Human μ-calpain is isolated from erythrocytes following the methods of Croall and DeMartino (BBA 1984, Vol. 788, 348–355) and Graybill et al. (Bioorg. & Med. Lett. 1995, Vol. 5, 387–392). After several chromatographic steps (DEAE Sepharose, phenyl Sepharose, Superdex 200 and Blue Sepharose), the enzyme is obtained at a purity of <95%, as assessed by SDS-PAGE, Western Blot analysis and N-terminal sequencing. The fluorescence of the cleavage product 7-amino-4-methylcoumarin (AMC) is followed in a Spex-Fluorolog fluorimeter at $\lambda_{ex}$=380 nm and $\lambda_{em}$=460 nm. If the experiments are carried out at temperatures of 12° C., the cleavage of the substrate is linear, and the autocatalytic activity of calpain is low, over a measurement period of 60 min (see Chatterjee et al. 1996, Bioorg. & Med. Chem. Lett., Vol 6, 1619–1622). The inhibitors and the calpain substrate are added to the experimental mixture as DMSO solutions, in association with which the final concentration of the DMSO should not exceed 2%.

In a typical experimental mixture, 10 μl of substrate (250 μm finally) and then 10 μl of μ-calpain (2 μg/ml finally, i.e. 18 nM) are added to a 1 ml cuvette which contains buffer. The calpain-mediated cleavage of the substrate is measured for from 15 to 20 min. 10 μl of inhibitor (50 or 100 μM solution in DMSO) are then added and inhibition of the cleavage is measured for a further 40 min. K$_i$ values are determined using the customary equation for reversible inhibition, ie. K:=1(v$_o$/v$_1$)-1; where I=inhibitor concentration, v$_o$=initial velocity before adding the inhibitor; v$_i$=reaction velocity at equilibrium.

Calpain is an intracellular cysteine protease. Calpain inhibitors have to pass through the cell membrane in order to prevent the degradation of intracellular proteins by calpain. Some known calpain inhibitors, such as E 64 and leupeptin, are only able to traverse the cell membranes with difficulty and correspondingly have only a poor effect on cells even though they are good inhibitors of calpain. The aim is to find compounds which are better able to pass through membranes. In the present case, human platelets are used for demonstrating the ability of calpain inhibitors to pass through membranes.

Calpain-mediated Degradation of Tyrosine Kinase pp60src in Platelets

Tyrosine kinase pp60src was cleaved by calpain after platelets had been activated. This was investigated in detail by Oda et al. in J. Biol. Chem., 1993, Vol 268, 12603–12608. This study showed that the cleavage of pp60src can be prevented by calpeptin, which is an inhibitor of calpain. The cellular efficacy of the novel substances was tested in accordance with this publication. Fresh human, citrate-treated blood was centrifuged at 200 g for 15 min. The platelet-rich plasma was pooled and diluted 1:1 with platelet buffer (platelet buffer: 68 mM NaCl, 2.7 mM KCl, 0.5 mM MgCl$_2$×6 H$_2$O, 0.24 mM NaH$_2$PO$_4$×H$_2$O, 12 mM NaHCO$_3$, 5.6 mM glucose, 1 mM EDTA, pH 7.4). After a centrifugation and washing step using platelet buffer, the platelets were adjusted to 10$^7$ cells/ml. The human platelets were isolated at RT.

In the test mixture, isolated platelets (2×10$^6$) were preincubated, at 37° C. for 5 min, with different concentrations of inhibitors (dissolved in DMSO). The platelets were then activated with 1 μM ionophore A23187 and 5 mM CaCl$_2$. After 5 min of incubation, the platelets were centrifuged briefly at 13,000 rpm and the pellet was taken up in SDS sample buffer (SDS sample buffer: 20 mM Tris-HCl, 5 mM EDTA, 5 mM EGTA, 1 mM DTT, 0.5 mM PMSF, 5 μg/ml leupeptin, 10 μm pepstatin, 10% glycerol and 1% SDS). The proteins were fractionated in a 12% strength gel, and pp60src and its 52 kDa and 47 kDa cleavage products were identified by Western Blotting. The polyclonal rabbit anti-Cys-src (pp60$^{c-src}$) antibody was obtained from Biomol Feinchemikalien (Hamburg). This primary antibody was detected with a second goat HRP-coupled antibody (Boehringer Mannheim, FRG). The Western Blotting was carried out in accordance with known methods.

The cleavage of pp60src was quantified densitometrically, with the controls employed being non-activated platelets (control 1: no cleavage) and platelets which were treated with ionophore and calcium (control 2: corresponds to 100% cleavage). The ED$_{50}$ value corresponds to the concentration of inhibitor at which the intensity of the color reaction of the 60 kDa band corresponds to the value: intensity of control 1 plus control 2 divided by 2.

Calpain is also postulated to play a role in apoptotic cell death (M. K. T. Squier et al. J.Cell.Physiol. 1994, 159, 229–237; T. Patel et al. Faseb Journal 1996, 590, 587–597). For this reason, cell death was triggered in another model, a human cell line, using calcium in the presence of a calcium ionophore. Calpain inhibitors have to get into the cell, and once there inhibit calpain, in order to prevent the cell death which has been triggered.

Calcium-mediated Cell Death in NT2 Cells

In the human cell line NT2, cell death can be triggered by calcium in the presence of the ionophore A 23187. 20 h before the experiment, $10^5$ cells are plated out per well in microtiter plates. After this period, the cells are incubated together with differing concentrations of inhibitors in the presence of 2.5 μM ionophore and 5 mM calcium. After 5 h, 0.05 ml of XTT (Cell Proliferation Kit II, Boehringer Mannheim) is added to the reaction mixture. The optical density is determined, about 17 h later, in an SLT EASY READER EAR 400 in accordance with the manufacturer's instructions. The optical density at which half the cells have died is calculated from the two measurements of the samples without inhibitors which were incubated in the absence and in the presence of ionophore.

Increased glutamate activity, which leads to states of superexcitement or toxic effects in the central nervous system (CNS), occurs in a number of neurological diseases or psychic disturbances.

Consequently, substances which inhibit the glutamate-mediated effects can be used to treat these diseases. Glutamate antagonists, which also, in particular, include NMDA antagonists and their modulators and the AMPA antagonists, are suitable for therapeutic use as agents against neurodegenerative diseases (Huntington's chorea and Parkinson's diseases), neurotoxic disturbances following hypoxia, anoxia or ischemia, as occur following a stroke, or else as antiepileptics, antidepressives and anxiolytics (cf. Arzneim. Forschung 1990, 40, 511–514; TIPS, 1990, 11, 334–338 and Drugs of the Future 1989, 14 (11), 1059–1071).

Intracerebral administration of excitatory amino acids (EAA) induces a superexcitation which is so massive that it rapidly leads to convulsions and the death of the animal. These symptoms can be inhibited by the systemic, eg. intraperitoneal, administration of centrally acting EAA antagonists. Since excessive activation of EAA receptors in the central nervous system plays an important role in the pathogenesis of various neurological diseases, it can be concluded that substances which are demonstrated to exhibit EAA antagonism in vivo will be useful in the therapy of CNS diseases of this nature. These diseases include, inter alia, focal and global ischemias, trauma, epilepsies and various neurodegenerative diseases such as Huntington's chorea, Parkinson's disease, inter alia.

It has already been shown that calpain inhibitors, too, exhibit a protective effect against EAA-induced cell death in cell cultures (H. Cauer et al., Brain Research 1993, 607, 354–356; Yu Cheg and A. Y. Sun, Neurochem. Res. 1994, 19, 1557–1564). Surprisingly, the calpain inhibitors mentioned in this application are effective even against the convulsions which are induced by EAA (eg. NMDA or AMPA) and consequently point to a therapeutic use in the abovementioned CNS diseases.

Glutamate-induced Cell Death in Cortical Neurones

The test was carried out as described in Choi D. W., Maulucci-Gedde M. A. and Kriegstein A. R., "Glutamate neurotoxicity in cortical cell culture". J. Neurosci. 1989, 7, 357–368.

The cortex halves are dissected out of 15 day-old mouse embryos and the individual cells are obtained enzymically (trypsin) These cells (glia and cortical neurones) are sown in 24-well plates. After three days (laminin-coated plates) or 7 days (ornithine-coated plates), mitosis treatment is carried out using FDU (5-fluoro-2-deoxyuridine). 15 days afer the cell preparation, cell death is induced by adding glutamate (15 min). The calpain inhibitors are added after the glutamate has been removed. 24 h later, cell damage is ascertained by determining lactate dehydrogenase (LDH) in the cell culture supernatant.

The benzamides of the formula I are inhibitors of cysteine proteases such as, in particular, calpain I and calpain II and cathepsin B and cathepsin L, and may consequently be used for controlling diseases which are associated with an increase in the activity of the calpain enzymes or the cathepsin enzymes. They are therefore useful for treating neurodegenerative diseases which occur following ischemia, trauma, subarachnoid hemorrhage and stroke, and which include, in particular, cerebral stroke and cranial trauma, and neurodegenerative diseases such as multiple infarction dementia, Alzheimer's disease and Huntington's disease, and, furthermore, are used for treating damage to the heart following cardiac ischemias, damage to the kidneys following renal ischemias, skeletal muscle damage, muscular dystrophies, damage which occurs due to proliferation of the smooth muscle cells, coronary vasospasms, cerebral vasospasms, cataracts of the eyes and restenosis of the blood vessels following angioplasty. In addition, the benzamaides of the formula I can be of use in the chemotherapy of tumors and their metastases and are used for treating diseases in which there is an elevated level of interleukin-1, as in the case of inflammations and rheumatic disorders.

In addition to the customary drug auxiliaries, the drug preparations according to the invention comprise a therapeutically effective quantity of the compounds I.

For local external use, for example in powders, ointments or sprays, the active compounds can be present in the customary concentrations. As a rule, the active compounds are present in a quantity of from 0.001 to 1% by weight, preferably of from 0.01 to 0.1% by weight.

In the case of internal use, the preparations are administered in single doses. In a single dose, from 0.1 to 100 mg are administered per kg of body weight. The preparations may be administered daily in one or more dosages depending on the nature and severity of the disorders.

In addition to the active compound, the drug preparations according to the invention comprise the customary carrier substances and diluents in accordance with the desired type of application. For local external applications, use can be made of pharmaceutical auxiliary substances such as ethanol, isopropanol, ethoxylated castor oil, ethoxylated hydrogenated castor oil, polyacrylic acid, polyethylene glycol, polyethylene glycostearate, ethoxylated fatty alcohols, paraffin oil, vaseline and lanolin. For internal applications, lactose, propylene glycol, ethanol, starch, talc and polyvinylpyrrolidone are suitable, for example.

Antioxidants, such as tocopherol and butylated hydroxyanisole and also butylated hydroxytoluene, taste-improving additives, stabilizers, emulsifiers and lubricants may also be present.

The substances which are contained in the preparation in addition to the active compound, and also the substances which are used in producing the pharmaceutical preparations, are toxicologically harmless and compatible with the relevant active compound. The drug preparations are produced in a customary manner, for example by mixing the active compound with other customary carrier substances and diluents.

The drug preparations may be administered in a variety of application modes, for example perorally, parenterally, such as intravenously by infusion, subcutaneously, intraperitoneally and topically. Thus, possible preparation forms include tablets, emulsions, infusion solutions, injection solutions, pastes, ointments, gels, creams, lotions, powders and sprays.

EXAMPLES

Example 1

2-(4-(N-(S)-3-Phenylpropan-1-al-2-yl)carbamoylphenyl)benzo-[g]phthalimide

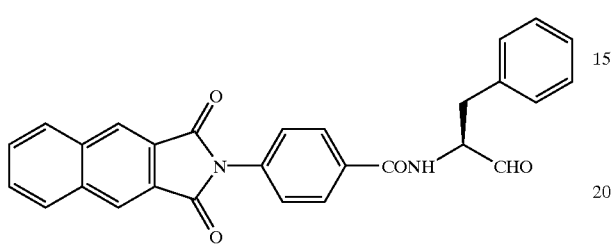

a) 2-(4-Ethoxycarbonylphenyl)benzo[g]phthalimide 10 g (50 mmol) of naphthalene-2,3-dicarboxylic anhydride and 8.3 g (50 mmol) of ethyl 3-aminobenzoate were heated at 90° C. for 16 h in 50 ml of n-butanol. The mixture was allowed to cool down and the precipitate, which had separated out, was then filtered off with suction. Yield: 8.4 g (48%).

b) 2-(4-Carboxyphenyl)benzo[g]phthalimide 7.6 g (22 mmol) of the intermediate compound 1a were dissolved in 100 ml of ethanol and, after 50 ml of 2M sodium hydroxide solution had been added, the mixture was stirred at room temperature for 16 h. The organic solvent was removed under reduced pressure and the aqueous residue was acidified with 1M hydrochloric acid. The precipitate which separated out during this procedure was filtered off with suction. Yield: 7.2 g (100%).

c) 2-(4-(N-(S)-3-Phenylpropan-1-ol-2-yl)carbamoylphenyl)-benzo[g]phthalimide 1.9g (18.8 mmol) of triethylamine, 25 ml of dimethyl sulfoxide and 0.34 g (2.5 mmol) of 1-hydroxybenzotriazole (HOBT) were added consecutively to 2.4 g (7.5 mmol) of the intermediate compound 1b and 1.1 g (7.5 mmol) of (S)-3-phenylalaninol in 50 ml of anhydrous methylene chloride. 1.4 g (7.5 mmol) of 3-(3-dimethylaminopropyl)-1-ethylcarbodiimide hydrochloride (EDC) were then added at 0° C. The whole was stirred at 0° C. for 1 h and, after that, at room temperature for 16 h. The organic solvent was then removed under reduced pressure and the residue was diluted with 500 ml of water. The precipitate was filtered off with suction and purified by chromatography (mobile solvent: methylene chloride/methanol/triethylamine=3/1/1), resulting in 1.0 g (30%) of the product.

d) 2-(4-(N-(S)-3-Phenylpropan-1-al-2-yl)carbamoylphenyl)-benzo[g]phthalimide 1.15 g (7.2 mmol) of pyridine-sulfur trioxide complex, dissolved in 20 ml of dimethyl sulfoxide, were added, at room temperature, to 0.8 g (1.8 mmol) of the intermediate compound 1c and 0.73 g (7.2 mmol) of triethylamine in 20 ml of anhydrous dimethyl sulfoxide. The whole was stirred at room temperature for 16 h. The reaction mixture was poured onto 500 ml of water and the resulting precipitate was filtered off with suction. Yield: 0.7 g (89%).

1H NMR (D$_6$-DMSO): δ=3.0(1H), 3.3(1H), 4.5(1H), 7.1–8.4(13H), 8.6(2H), 9.0(1H) and 9.6(1H)ppm

Example 2

6,7-Dimethoxy-3-(4-(N-(S)-3-phenylpropan-1-al-2-yl)carbamoyl-phenyl)benzopyrimidione

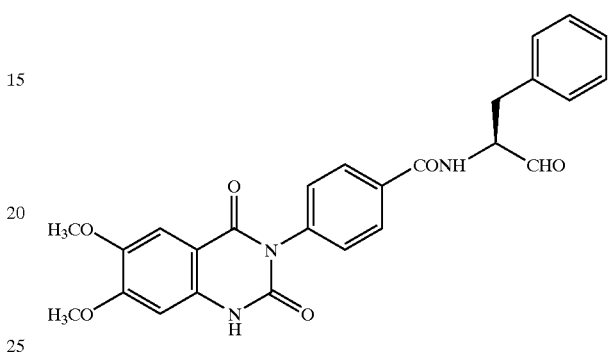

a) 6,7-Dimethoxy-3-(4-ethoxycarbonylphenyl)benzopyrimidione 15.4 g (80.5 mmol) of 4-ethoxycarbonylphenyl isocyanate were added in portions, at room temperature, to 17 g (80.5 mmol) of methyl 2-amino-4,5-dimethoxybenzoate and a spatula tip of 4-dimethylaminopyridine in 250 ml of anhydrous dimethylformamide. The whole was then stirred at 100° C. for 1 h. The solvent was removed under reduced pressure and the residue was heated to 180° C. The reaction mixture crystallized throughout after some time. After that, the solid material was treated with acetone and filtered off with suction. The solid material was then recrystallized from dimethylformamide, resulting in 21.5 g (73%) of the product.

b) 3-(4-Carboxyphenyl)-6,7-dimethoxybenzopyrimidione 21.5 g (58 mmol) of the intermediate compound 2a were suspended in 100 ml of tetrahydrofuran, after which 5.6 g (0.32 mol) of lithium hydroxide, dissolved in 300 ml of water, were added. The whole was stirred at room temperature for 2 h. After that, the reaction solution was acidified with 15 ml of glacial acetic acid and the organic solvent was removed under reduced pressure. The precipitate which resulted during this procedure was filtered off with suction, with 20.3 g (100%) of the product being obtained.

c) 6,7-Dimethoxy-3-(4-(N-(S)-3-phenylpropan-1-ol-2-yl)carbamoyl-phenyl)benzopyrimidione 2 g (5.8 mmol) of the intermediate compound 2b were reacted in a similar manner to that described in Example 1c in a solvent mixture consisting of dimethylformamide and dimethyl sulfoxide. Yield: 2.3 g (83%).

d) 6,7-Dimethoxy-3-(4-(N-(S)-3-phenylpropan-1-al-2-yl)carbamoyl-phenyl)benzopyrimidione 2.1 g (4.4 mmol) of the intermediate compound were oxidized in a similar manner to that described in Example 1d. Yield: 0.65 g (35%).

Example 3

2-(4-Methyl-3-(N-(S)-3-phenylpropan-1-al-2-yl)carbamoylphenyl)-benzo[g]phthalimide

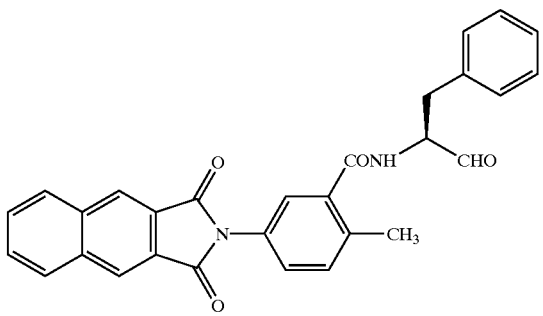

a) 2-Methyl-5-nitro-N-((S)-3-phenylpropan-2-yl-3-ol)benzamide 2.6 ml (27.6 mmol) of ethyl chloroformate, dissolved in 30 ml of tetrahydrofuran, were added dropwise, at 0° C., to 5 g (27.6 mmol) of 2-methyl-5-nitrobenzoic acid and 4.2 ml (30.4 mmol) of triethylamine in 70 ml of anhydrous tetrahydrofuran. The whole was stirred at room temperature for 1 h. After that, 4.2 g (27.6 mmol) of (S)-3-phenylalaninol were added and the whole was stirred at room temperature for 16 h. The mixture was then filtered and the filtrate was concentrated under reduced pressure. The residue was partitioned between ethyl acetate and water. The organic phase was then washed with an aqueous solution of sodium hydrogen carbonate, water, dilute hydrochloric acid and once again with water, dried and concentrated under reduced pressure. The residue was then treated with ether and filtered off with suction. 7.5 g (87%) of the intermediate compound were obtained.

b) 5-Amino-2-methyl-N-((S)-3-phenylpropan-2-yl-3-ol)benzamide 6.3 g (20 mmol) of the intermediate compound 3a were dissolved in 200 ml of ethanol/tetrahydrofuran (3/1) and hydrogenated after 0.5 g of palladium/carbon (10% strength) had been added. After that, the mixture was filtered and the filtrate was concentrated under reduced pressure. The residue was then treated with ether and filtered off with suction. Yield: 4.9 g (86%).

c) 2-(4-Methyl-3-(N-(S)-3-phenylpropan-1-ol-2-yl)carbamoyl-phenyl)benzo[g]phthalimide 0.76 g (4 mmol) of the intermediate compound 3b was reacted, in a similar manner to that described in Example 1a with naphthalene-2,3-dicarboxylic anhydride, resulting in 0.59 g (48%) of the product.

d) 2-(4-Methyl-3-(N-(S)-3-phenylprbpan-1-al-2-yl)carbamoyl-phenyl)benzo[g]phthalimide 0.42 g (0.9 mmol) of the intermediate compound 3c was oxidized in a similar manner to that described in Example 1d. Yield: 0.34 g (81%).

1H NMR (D$_6$-DMSO): δ=2.2(3H), 2.8(1H), 3.4(1H), 4.7 (1H), 7.1–7.6(8H), 7.8(2H), 8.3(2H), 8.6(2H), 8.8(1H) and 9.7 (1H)ppm.

MS: M/e=473 (M$^+$).

Example 4

2-(4-(N-(S)-3-Phenylpropan-1-al-2-yl)carbamoylphenyl)methyl-benzo[g]-phthalimide

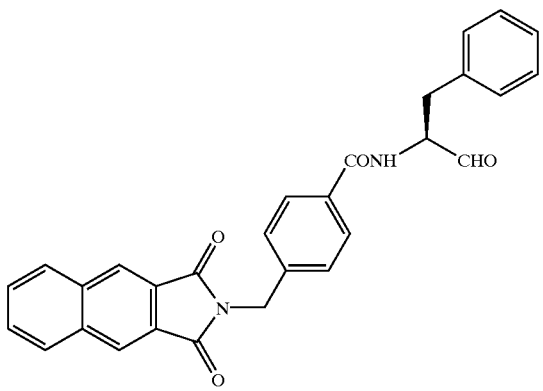

a) 2-(4-Ethoxycarbonylphenyl)methylbenzo[g]phthalimide 1.7 g (10 mmol) of ethyl 4-aminomethylbenzoate hydrochloride and 2.0 g (20 mmol) of triethylamine were stirred at room temperature for 15 min in 25 ml of PEG400. After that, 2 g (10 mmol) of 2,3-naphthalenedicarboxylic anhydride were added and the whole was heated at 100° C. for 2 h. The reaction mixture was subsequently added to water and the precipitate was filtered off with suction. 2.3 g (68 %) of the intermediate compound were obtained.

b) 2-(4-Carboxyphenyl)methylbenzo[g]phthalimide 2 g (5.8 mol) of the intermediate compound 4a were hydrolyzed in a similar manner to that described in Example 1b. Yield: 1.9 g (98%).

c) 2-(4-(N-(S)-3-Phenylpropan-1-ol-2-yl)carbamoylphenyl)methyl-benzo[g]phthalimide 1.3 g (4 mmol) of the intermediate compound 4b were reacted in a similar manner to that described in Example 1c. Yield: 0.65 g (35%).

d) 2-(4-(N-(S)-3-Phenylpropan-1-al-2-yl)carbamoylphenyl)methyl-benzo[g]phthalimide 0.33 g (0.7 mmol) of the intermediate compound 4c were oxidized in a similar manner to that described in Example 1d. Yield: 0.3 g (97%).

MS (ESI): m/e=462 (M$^+$).

Example 5

3-(4-(N-(S)-3-Phenylpropan-1-al-2-yl)carbamoylphenyl)naphtho[c]-pyrimidione

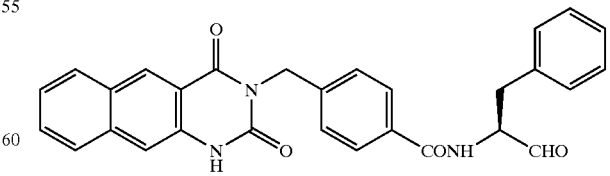

a) 3-(4-Ethoxycarbonylphenyl)naphtho[c]pyrimidione 1.4 g (7 mmol) of ethyl 3-aminonaphthoate, 1.34 g (7 mmol) of 4-ethoxyphenyl isocyanate and a spatula tip of 4-dimethylaminopyridine were refluxed for 4 h in 30 ml of tetrahydrofuran. The whole was then concentrated under reduced pressure and the residue was decocted with ethanol and filtered off with suction. Yield: 1.7 g (67%).

b) 3-(4-Carboxyphenyl)naphtho[c]pyrimidione 1.6 g (4.4 mmol) of the intermediate compound 5a were added to 30 ml of tetrahydrofuran, after which 0.8 g (28.9 mmol) of lithium hydroxide, dissolved in 30 ml of water, 12 ml 2 ml [sic] of 2M sodium hydroxide solution and 30 ml of ethanol were added and the whole was stirred at room temperature for 1 h. The organic solvent was concentrated in vacuo and the remaining aqueous phase was diluted and acidified to a pH of approx. 2–3 with dilute hydrochloric acid. The precipitate was filtered off with suction, resulting in 1.4 g (96%) of the product.

c) 3-(4-(N-(S)-3-Phenylpropan-1-ol-2-yl) carbamoylphenyl)-naphtho[c]-pyrimidione 1.3 g (4 mmol) of the intermediate compound 5b were reacted in a similar manner to that described in Example 1c. Yield: 1.1 g.

d) 3-(4-(N-(S)-3-Phenylpropan-1-al-2-yl) carbamoylphenyl)-naphtho[c]-pyrimidione 0.9 g (2 mmol) of the intermediate compound 5c were oxidized in a similar manner to that described in Example 1d, resulting in 0.65 g (72%) of the product.

1H NMR (D$_6$-DMSO): δ=2.95 (1H), 3.2(1H), 4.5(1H), 7.1–8.1(1H), 8.7(1H), 9.0(1H), 9.6(1H) and 11.7(1H)ppm.

Example 6

3-(4-(N-((S)-1-Carbamoyl-1-oxo-3-phenylpropan-2-yl)carbamoyl-phenyl)-naphtho[c]pyrimidione

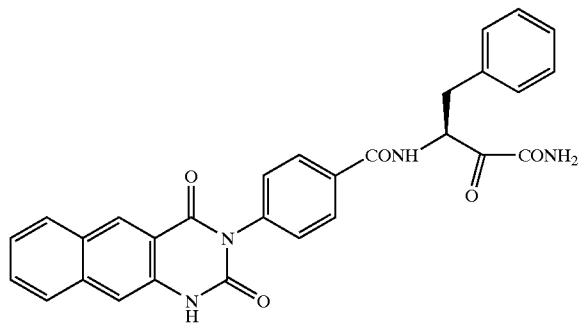

a) 3-(4-(N-(2-(S)-1-Carbamoyl-1-hydroxy-3-phenylpropan-2-yl)-carbamoylphenyl)naphtho[c] pyrimidione 1.2 g (3.6 mmol) of the intermediate compound 5b were reacted, in a similar manner to that described in Example 1c with 1.1 g (3.6 mmol) of O-(tert-butyl)-2(S)-N-(1-carboxy-2-hydroxy-3-phenylpropan-1-ol-2-yl)carbamate (S. L. Harbeson et al., J.Med.Chem. 1994, 37, 2918–29). Yield: 1.2 g (66%).

b) 3-(4-(N-((S)-1-Carbamoyl-1-oxo-3-phenylpropan-2-yl)-carbamoyl phenyl)naphtho[c] pyrimidione 1.1 g (2.2 mmol) of the intermediate compound 6a were oxidized in a similar manner to that described in Example 1d. Yield: 0.93 g (90%).

MS: m/e 506 (M$^+$).

Example 7

8-Methyl-3-(4-(N-(S)-3-phenylpropan-1-al-2-yl) carbamoylphenyl)-benzopyrimidione

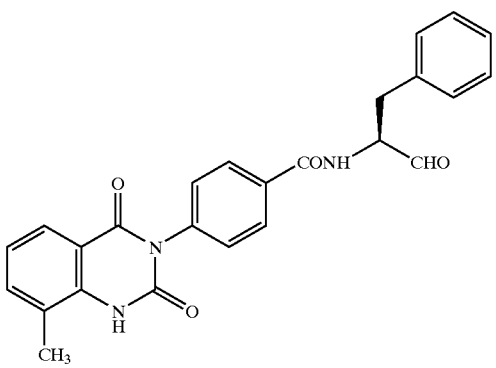

a) 3-(4-Ethoxycarbonylphenyl)-8-methylbenzopyrimidione 20 g (0.12 mol) of methyl 2-amino-5-methylbenzoate were reacted, in a similar manner to that described in Example 2a, with 4-ethoxycarbonylphenyl isocyanate. Yield: 30.1 g (77%).

b) 3-(4-carboxyphenyl)-8-methylbenzopyrimidione 29 g (89.4 mmol) of the intermediate compound 7a were hydrolyzed in a manner similar to that described in Example 2b, resulting in 21.3 g (81%) of the product.

c) 8-Methyl-3-(4-(N-(S)-3-phenylpropan-1-ol-2-yl) carbamoyl-phenyl)benzopyrimidione 2 g (6.8 mmol) of the intermediate compound 7b were reacted in a manner similar to that described in Example 1c. Yield: 1.5 g (52%).

d) 8-Methyl-3-(4-(N-(S)-3-phenylpropan-1-al-2-yl) carbamoyl-phenyl)benzopyrimidione 1.3 g (3.0 mmol) of the intermediate compound 7c were reacted in a manner similar to that described in Example 2d. Yield: 1.2 g (93%).

1H NMR (D$_6$-DMSO): δ=2.4(3H), 3.0(1H), 3.4(lH), 4.5 (1H), 7.0–8.0(12H), 9.0(1H), 9.6(1H) and 11.9(1H)ppm.

Example 8

3-(4-(N-(S)-3-Phenylpropan-1-al-2-yl)carbamoylphenyl)benzo-pyrimidione

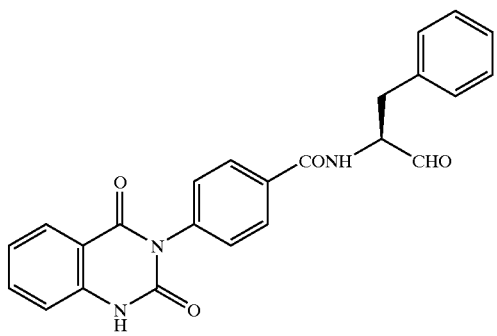

a) 3-(4-Ethoxycarbonylphenyl)benzopyrimidione 19 g (0.1 mol) of propyl 2-aminobenzoate were reacted, in a manner similar to that described in Example 2a, with 4-ethoxycarbonylphenyl isocyanate, resulting in 12.2 g (32%) of the product.

b) 3-(4-Carboxyphenyl)benzopyrimidione 30 g (92.5 mmol) of the intermediate compound 8a were hydrolyzed in a similar manner to that described in Example 2b. Yield: 25.1 g (92%).

c) 3-(4-(N-(S)-3-Phenylpropan-1-ol-2-yl)carbamoylphenyl)benzo-pyrimidione 2 g (7.1 mmol) of the intermediate compound 8b were reacted in a similar manner to that described in Example 1c. Yield: 2.6 g (88%).

d) 3-(4-(N-(s)-3-Phenylpropan-1-al-2-yl)carbamoylphenyl)benzo-pyrimidione 2.3 g (55.4 mmol) of the intermediate compound 8c were reacted in a similar manner to that described in Example 1d. Yield: 1.7 g (74%).

1H NMR ($D_6$-DMSO): 67 =3.0(1H), 3.3(1H), 4.5(1H), 7.0–8.0(13H), 9.0(1H), 9.7(1H) and 11.6 (1H) ppm.

Example 9

6-Methyl-3-(4-(N-(S)-3-phenylpropan-1-al-2-yl)carbamoylphenyl)-benzopyrimidione

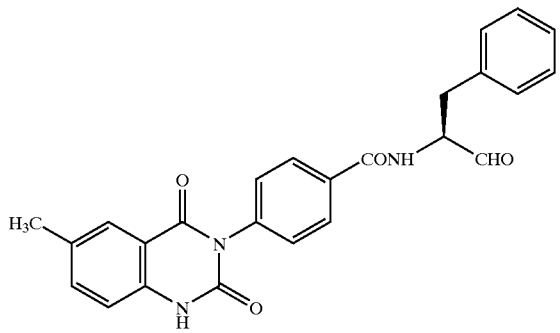

a) 3-(4-Ethoxycarbonylphenyl)-6-methylbenzopyrimidione 20 g (0.12 mol) of methyl 2-amino-5-methylbenzoate were reacted, in a manner similar to that described in Example 2a with 4-ethoxycarbonylphenyl isocyanate, resulting in 30.1 g (77%) of the product.

b) 3-(4-Carboxyphenyl)-6-methylbenzopyrimidione 30 g (92.5 mmol) of the intermediate compound 9a were hydrolyzed in a similar manner to that described in Example 2b. Yield: 25.1 g (92%).

c) 6-Methyl-3-(4-(N-(S)-3-phenylpropan-1-ol-2-yl)carbamoyl-phenyl)benzopyrimidione 2 g (6.8 mmol) of the intermediate compound 9b were reacted in a similar manner to that described in Example 1c. Yield: 1.2 g (42%).

d) 6-Methyl-3-(4-(N-(S)-3-phenylpropan-1-al-2-yl)carbamoyl-phenyl)benzopyrimidione 1.0 g (2.3 mmol) of the intermediate compound 9c were reacted in a similar manner to that described in Example 1d. Yield: 0.73 g (73%).

1H NMR ($D_6$-DMSO): δ=2.4(3H), 3.0(1H), 3.3(1H), 4.5(1H), 7.0–8.0(12H), 9.0(1H), 9.7(1H) and 11.5(broad)ppm.

Example 10

7-Chloro-3-(4-(N-(S)-3-phenylpropan-1-al-2-yl)carbamoylphenyl)-benzopyrimidione

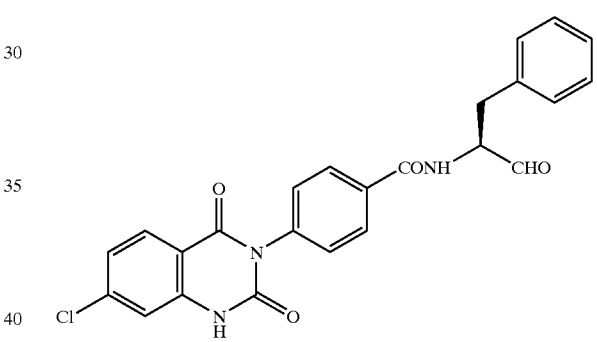

a) 7-Chloro-3-(4-ethoxycarbonylphenyl)benzopyrimidione 16 g (86.2 mmol) of methyl 2-amino-4-chlorobenzoate were reacted, in a similar manner to that described in Example 2a, with 4-ethoxycarbonylphenyl isocyanate, resulting in 12.1 g (41%) of the product.

b) 3-(4-Carboxyphenyl)-7-chlorobenzopyrimidione 12 g (34.8 mmol) of the intermediate compound 10a were hydrolyzed in a similar manner to that described in Example 2b. Yield: 10.1 g (91%).

c) 7-Chloro-3-(4-(N-(S)-3-phenylpropan-1-ol-2-yl)carbamoyl-phenyl)benzopyrimidione 2 g (6.3 mmol) of the intermediate compound 10b were reacted in a similar manner to that described in Example 1c. Yield: 1.7 g (60%).

d) 7-Chloro-3-(4-(N-(S)-3-phenylpropan-1-al-2-yl)carbamoyl-phenyl)benzopyrimidione 1.3 g (28.9 mmol) of the intermediate compound 10c were reacted in a similar manner to that described in Example 1d. Yield: 1.1 g (86%).

1H NMR (D$_6$-DMSO): δ=3.0(1H), 3.3(1H), 4.5(1H), 7.0–8.0 (12H), 9.0(1H), 9.7 (1H) and 11.7(1H)ppm.

The following were prepared in analogy with Examples 1–10:

Example 11

3-(4-(N-(S)-Pent-1-al-2-yl)carbamoylphenyl) naphtho[c]pyrimidione

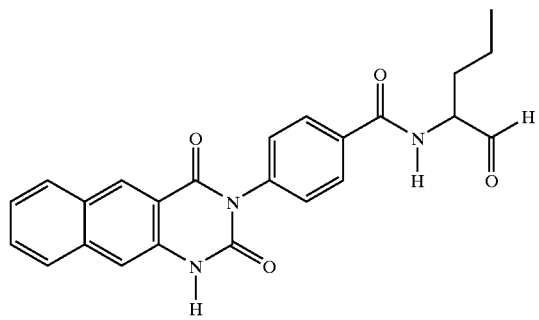

$^1$H NMR (D$_6$-DMSO): δ=0.9 (3H), 1.45 (2H), 1.7 (1H), 1.9 (1H), 4.3 (1H), 7.4–7.8 (5H), 7.9–8.2 (4H), 8.7 (1H), 9.0 (1H), 9.6 (1H), 11.7 (1H).

Example 12

3-(4-(N-(S)-Cyclohexylprop-1-al-2-yl) carbamoylphenyl)naphtho-[c]pyrimidione

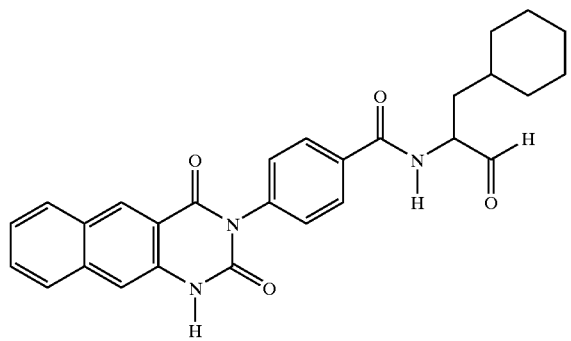

$^1$H NMR (D$_6$-DMSO): δ=0.8–2.0 (13H), 4.4 (1H), 7.4–7.7 (5H), 7.8–8.2 (4H), 8.7 (1H), 9.6 (1H), 11.7 (1H).

Example 13

3-(4-(N-(S)-Ethylcarbamoyl-1-oxo-3-phenylpropan-2-yl)carbamoyl-phenyl)naphtho[c]pyrimidione

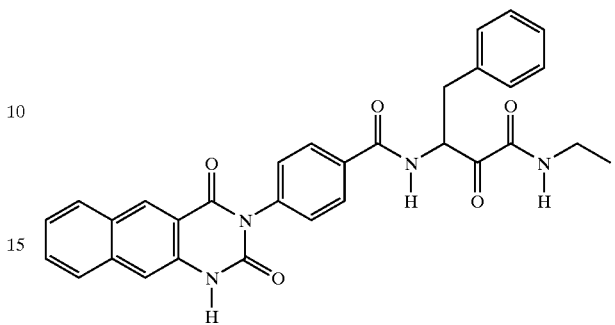

MS m/e=534 (M$^+$)

Example 14

3-(4-(N-(S)-(1-(2-Pyridyl)ethylcarbamoyl-1-oxo-3-phenylpropan-2-yl)carbamoylphenyl)naphtho[c] pyrimidione

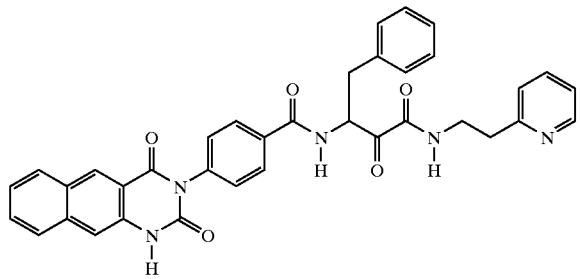

MS m/e=611 (M$^+$)

Example 15

3-(4-(N-(S)-3-Phenylprop-1-al-2-yl) carbamoylphenyl)pyrazino-[b]pyrimidione

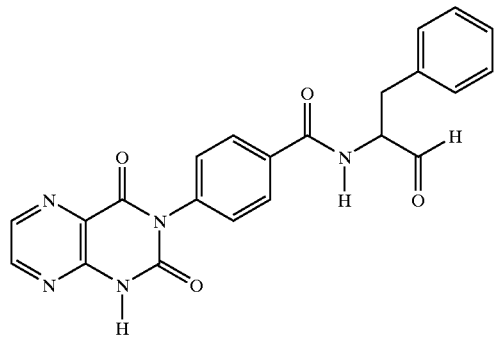

$^1$H NMR (D$_6$-DMSO): δ2.8–3.0 (2H), 4.5 (1H), 7.2–7.7 (5H), 7.6–7.9 (4H), 8.15 (1H9; 8.2) (1H), 8.8 (1H), 9.6 (1H).

Example 16

3-(4-(N-(S)-3-Phenylprop-1-al-2-yl)carbamoylphenyl)dichloro-pyrazino[b]pyrimidione

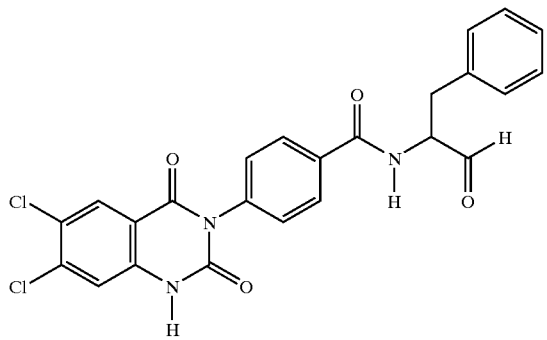

$^1$H NMR (D$_6$-DMSO): δ=2.9 (1H), 3.2 (1H), 4.4 (1H), 7.1 (5H), 7.5 (2H), 7.7 (2H), 8.8 (1H), 9.05 (1H), 9.6 (1H).

Example 17

5,7-Dimethyl-3-(4-(N-(S)-3-phenylprop-1-al-2-yl)carbamoylphenyl)-pyidino[b]pyrimidione

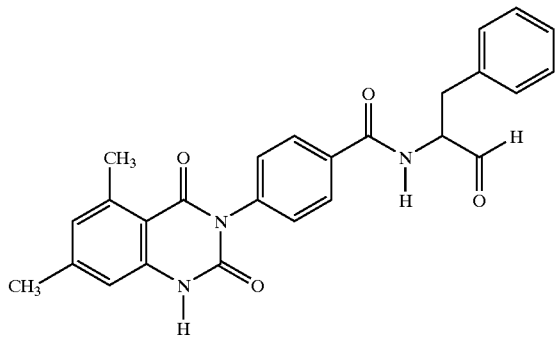

$^1$H NMR (D$_6$-DMSO): δ=2.45 (3H), 2.6 (3H), 3.0 (1H), 3.3 (1H), 3.3 (1H, 4.5 (1H), 7.01 (1H), 7.2–7.5 (7H), 7.9 (2H), 9.0 (1H), 9.6 (1H), ca. 12 (1H).

Example 18

3-(4-(N-(S)-3-(2-Pyridyl)prop-1-al-2-yl)carbamoylphenyl)naphtho-[c]pyrimidione

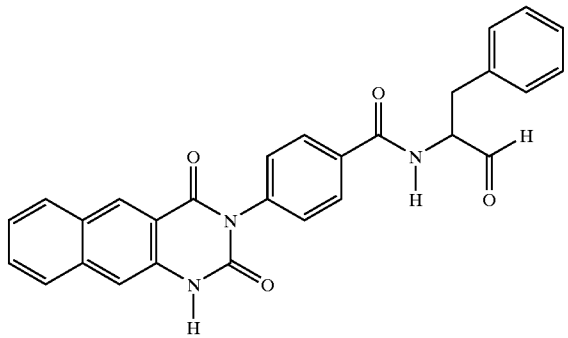

$^1$H NMR (D$_6$-DMSO): δ=2.8–3.3 (2H), 4.6 (1H), 7.2–8.2 (11H), 8.5 (1H), 8.7 (2H), 9.1 (1H), 9.6 (1H), 11.8 (broad, 1H).

Example 19

3-(4-(N-(S)-3-Phenylprop-1-al-2-yl)carbamoylphenyl)pyidino-[c]pyrimidione

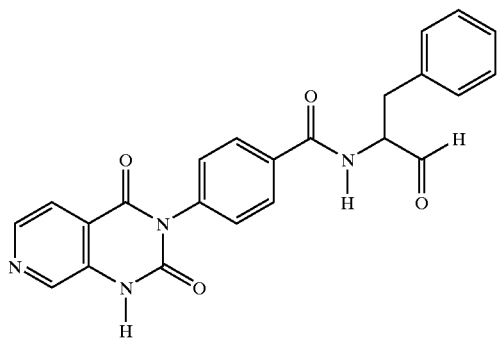

MS m/e=414 (M$^+$)

The following can be prepared in an analogous manner:

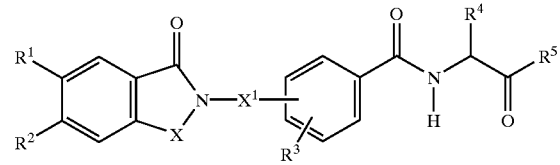

I

| No. | R$^1$ | R$^2$ | X | R$^3$ | -X$^1$- | R$^4$ | R$^5$ |
|---|---|---|---|---|---|---|---|
| 20 | H | H | —NHCO— | 4-Cl | 3- | benzyl | H |
| 21 | H | H | —NHCO— | 4-Me | 3- | pyridylmethyl | H |

-continued
| | | | | | | | | |
|---|---|---|---|---|---|---|---|---|
| 22 | H | H | —NHCO— | H | 3- | 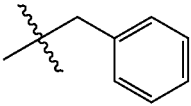 | | CONH₂ |
| 23 | Cl | H | —NHCO— | H | 4- | 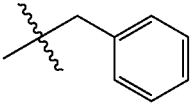 | | CONH₂ |
| 24 | —(CH₂)₄— | | —CO— | H | 4-CH₂ | 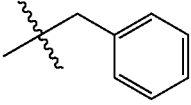 | | H |
| 25 | —(CH₂)₄— | | —CO— | H | 4-CH₂ | 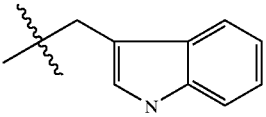 | | H |
| 26 | —(CH₂)₄— | | —CO— | H | 4-CH₂ | 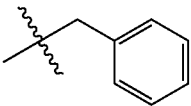 | | CONH₂ |
| 27 | —(CH₂)₄— | | —CO— | H | 4-CH₂ | 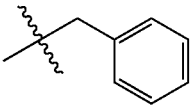 | | H |
| 28 | H | H | —CO— | 4-Me | 3- | 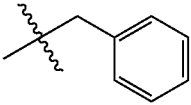 | | CONH₂ |
| 29 | H | H | —CO— | 4-Me | 3- | 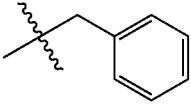 | | CONH—\/—N\_/O |
| 30 | MeO | MeO | —N=CH— | H | 3- | 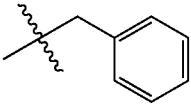 | | H |
| 31 | MeO | MeO | —N=CH— | H | 3- | 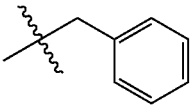 | | CONH₂ |
| 32 | MeO | MeO | —N=CH— | H | 3- | 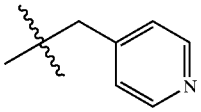 | | CONH—\/—N\_/O |
| 33 | —(CH₂)₄— | | —NHCO— | H | 4- | 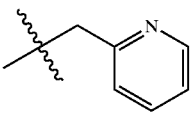 | | CONH₂ |

-continued

| | | | | | | | |
|---|---|---|---|---|---|---|---|
| 34 | —(CH$_2$)$_4$— | —NHCO— | 4-Cl | 3- | benzyl | | H |
| 35 | —(CH$_2$)$_4$— | —NHCO— | 4-Cl | 3- | cyclohexylmethyl | | H |
| 36 | —(CH$_2$)$_4$— | —NHCO— | 4-Cl | 3- | benzyl | | CONH$_2$ |
| 37 | —(CH$_2$)$_4$— | | CO | H | 4- | 4-hydroxybenzyl | H |
| 38 | —(CH$_2$)$_4$— | | CO | H | 3- | benzyl | H |
| 39 | —(CH$_2$)$_4$— | | CO | H | 3- | benzyl | CONHEt |
| 40 | —(CH$_2$)$_4$— | | CO | 2-Me | 4- | benzyl | CONH$_2$ |
| 41 | H | PhSO$_2$NH | —NHCO— | H | 2- | benzyl | H |
| 42 | H | Cl | —NHCO— | H | 2- | benzyl | H |
| 43 | H | NH$_2$ | —NHCO— | H | 2- | benzyl | CONH$_2$ |
| 44 | —(CH$_2$)$_4$— | | —CO— | H | 2- | benzyl | H |
| 45 | H | H | —CO— | H | 2- | benzyl | H |

-continued
| | | | | | | | |
|---|---|---|---|---|---|---|---|
| 46 | —(CH₂)₄— | —CO— | H | 2- | 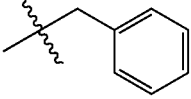 | | CONH₂ |
| 47 | MeO | MeO | —CO— | H | 2- | 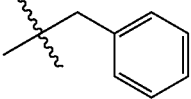 | CONH₂ |
| 48 | —(CH₂)₄— | | —N=CH | H | 2- | 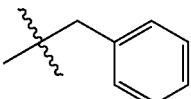 | CONH₂ |
| 49 | H | H | —N=CH | H | 2- | 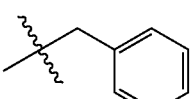 | CONH₂ |
| 50 | —(CH₂)₄— | | —N=CH | H | 2- | 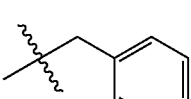 | H |
| 51 | —(CH₂)₄— | | —CO— | H | 2- | 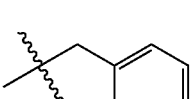 | H |
| 52 | H | NHCOCH₃ | —NHCO | H | 4- | 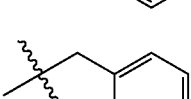 | CONH₂ |
| 53 | H | NHCOC₂H₅ | —NHCO | H | 4- | 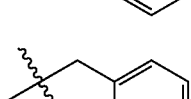 | CONH₂ |
| 54 | —(CH₂)₄— | | —N=CH— | H | 3- | 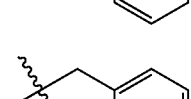 | CONH₂ |
| 55 | —(CH₂)₄— | | —N=CH— | H | 3- | 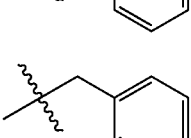 | CONHEt |
| 56 | —(CH₂)₄— | | —N=CH— | H | 3- | 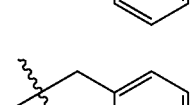 | CONH-CH₂CH₂-morpholine |
| 57 | —(CH₂)₄— | | —N=CH— | H | 3-CH₂ | 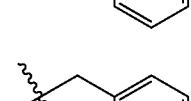 | CONH-CH₂CH₂-piperazine |
| 58 | H | H | —N=CH— | H | 4- | 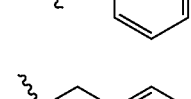 | H |

-continued
| | | | | | | | | |
|---|---|---|---|---|---|---|---|---|
| 59 | H | H | —N=CH— | H | 4- | 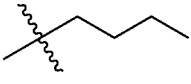 | | H |
| 60 | —(CH$_2$)$_4$— | | —CH$_2$CO— | H | 4- | 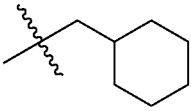 | | H |
| 61 | —(CH$_2$)$_4$— | | —CH$_2$CO— | H | 4-CH$_2$— | 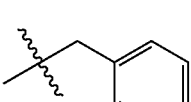 | | CONH$_2$ |
| 62 | H | Cl | —CH$_2$CO— | H | 4- | 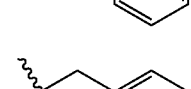 | | CONH$_2$ |
| 63 | H | H | —CH$_2$CO— | H | 4- | 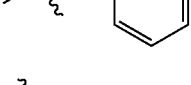 | | CONH$_2$ |
| 64 | Cl | H | —CH$_2$CO— | H | 4- | 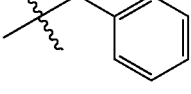 | | CONH$_2$ |
| 65 | —(CH$_2$)$_4$— | | —NHCO— | 2-NHCOCH$_3$ | 4- | 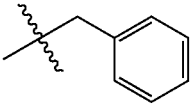 | | H |
| 66 | —(CH$_2$)$_4$— | | —NHCO— | 2-NHCOCH$_3$ | 4- | 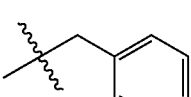 | | H |
| 67 | —(CH$_2$)$_4$— | | —NHCO— | 2-NHCOCH$_3$ | 4- | 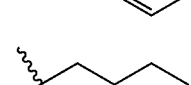 | | CONH—CH$_2$—COOH |
| 68 | Cl | H | —NHCO— | 4-Me | 3- | 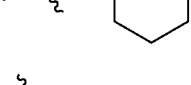 | | H |
| 69 | Cl | H | —NHCO— | H | 4-CH$_2$— | 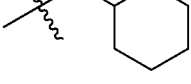 | | CONH$_2$ |
| 70 | H | Cl | —NHCO— | H | 4- | 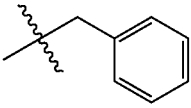 | | CONH$_2$ |
| 71 | H | NO$_2$ | —NHCO— | H | 4- | 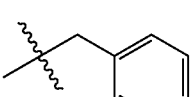 | | H |

-continued
| | | | | | | | |
|---|---|---|---|---|---|---|---|
| 72 | H | NO₂ | —NHCO— | H | 4- | 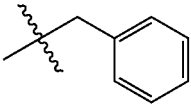 | H |
| 73 | MeO | MeO | —NHCO— | 4-Me | 3- | 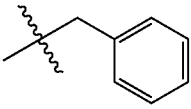 | CONH₂ |
| 74 | MeO | MeO | —NHCO— | 4-Me | 3- | 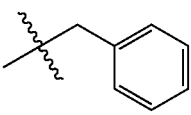 | 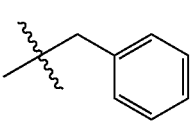 |
| 75 | MeO | MeO | —NHCO— | 4-Me | 3- | 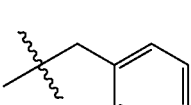 | 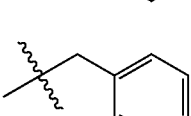 |
| 76 | H | PhSO₂NH | —NHCO— | H | 4- | 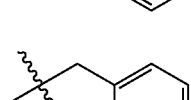 | CONH₂ |
| 77 | H | PhSO₂NH | —NHCO— | 2-Me | 4- | 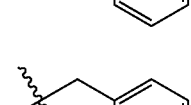 | H |
| 78 | H | H | —NHCO— | 2-NHCOCH₃ | 4- | 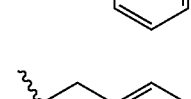 | CONH—COOH |
| 79 | H | H | —NHCO— | 2-NH₂ | 4- | 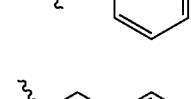 | H |
| 80 | H | H | —NHCO— | 2-NO₂ | 4- | | H |
| 81 | H | H | —NHCO— | 2-Cl | 4- | | H |
| 82 | H | H | —CH₂— | H | 4- | | H |
| 83 | H | H | —CH₂— | H | 4-CH₂ | 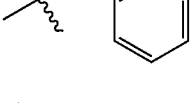 | H |

-continued
| | | | | | | | |
|---|---|---|---|---|---|---|---|
| 84 | —(CH$_2$)$_4$— | —CH$_2$— | 2-Me | 4- | 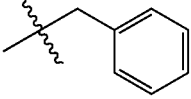 | H |
| 85 | —(CH$_2$)$_4$— | —CH$_2$— | 4-Me | 3- | 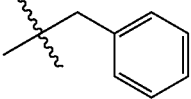 | H |
| 86 | —(CH$_2$)$_4$— | —NHCO— | H | 2- | 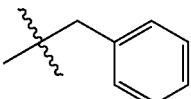 | H |
| 87 | —(CH$_2$)$_4$— | —NHCO— | H | 2- | 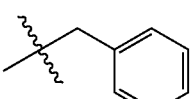 | CONH$_2$ |
| 88 | —(CH$_2$)$_4$— | —N=CH— | H | 3-CH$_2$ | 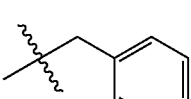 | 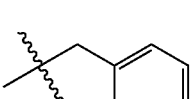 |
| 89 | —(CH$_2$)$_4$— | —N=CH— | H | 3-CH$_2$ | 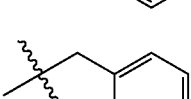 | H |
| 90 | —(CH$_2$)$_4$— | —N=CH— | 4-Me | 3- | 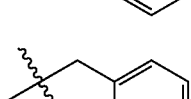 | CONH$_2$ |
| 91 | —(CH$_2$)$_4$— | —N=CH— | 4-Me | 3- | 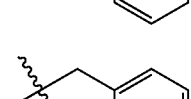 | H |
| 92 | H | PhSO$_2$NH | —NHCO— | H | 4-CH$_2$ | 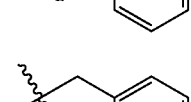 | H |
| 93 | H | NO$_2$ | —NHCO— | H | 4- | 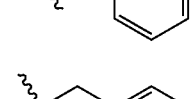 | H |
| 94 | H | CF$_3$ | —NHCO— | H | 4- | 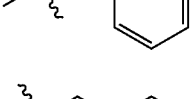 | H |
| 95 | H | PhSO$_2$ | —NHCO— | H | 4- | 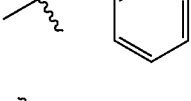 | H |
| 96 | H | COOH | —NHCO— | H | 4- | 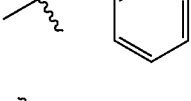 | H |

| | | | | | | | |
|---|---|---|---|---|---|---|---|
| 97 | H | COOH | —NHCO— | H | 4- | 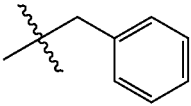 | H |
| 98 | H | NHCOPh | —NHCO— | H | 4- | 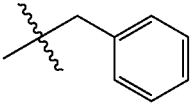 | CONH$_2$ |
| 99 | H | NHCOCH$_3$ | —NHCO— | 4-Me | 3- | 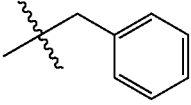 | CONH$_2$ |
| 100 | H | NHCOC$_2$H$_5$ | —NHCO— | 4-Me | 3- | 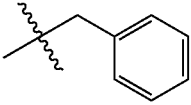 | CONH$_2$ |
| 101 | H | NHCOPh | —NHCO— | 4-Me | 3- | 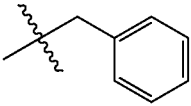 | CONH$_2$ |
| 102 | H | NHCOCH$_3$ | —CO— | H | 4- | 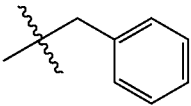 | CONH$_2$ |
| 103 | —(CH$_2$)$_4$— | | —NHCO— | H | 2- | 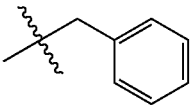 | CONHEt |
| 104 | H | PhSO$_2$ | —NHCO— | H | 2- | 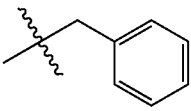 | CONH$_2$ |
| 105 | —(CH$_2$)$_4$— | | —N=CH— | 4-Me | 3- | 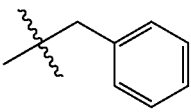 | CONH$_2$ |
| 106 | —(CH$_2$)$_4$— | | —N=CH— | 4-Me | 3- | 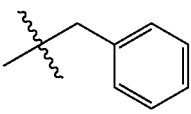 | CONHEt |
| 107 | —(CH$_2$)$_4$— | | —N=CH— | 4-Me | 3- | 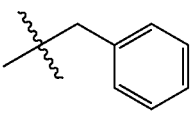 | CONHCH$_2$CH$_2$-(2-pyridyl) |
| 108 | H | H | —N=CH— | H | 4-CH$_2$ | 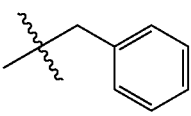 | piperidinyl-CO- |

-continued
| No. | R¹ | R² | X | R³ | | R⁴ | R⁵ |
|---|---|---|---|---|---|---|---|
| 109 | H | H | —N=CH— | H | 4-CH₂ | 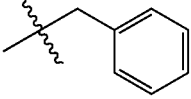 | H |
| 110 | —(CH₂)₄— | | —NHCO— | H | 3- | 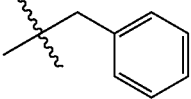 | H |
| 111 | —(CH₂)₄— | | —NHCO— | H | 3- | 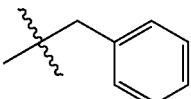 | CONH₂ |
| 112 | —(CH₂)₄— | | —NHCO— | H | 3- | 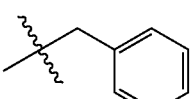 | CONH |
| 113 | —(CH₂)₄— | | —NHCO— | 4-Me | 3- | 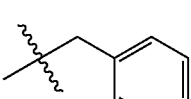 | CONH₂ |
| 114 | —(CH₂)₄— | | —NHCO— | 2-Me | 4- | 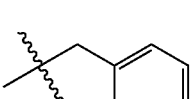 | H |
| 115 | —(CH₂)₄— | | —NHCO— | H | 4- | 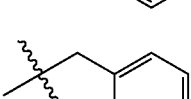 | CONH |
| 116 | —(CH₂)₄— | | —NHCO— | H | 4-CH₂ | 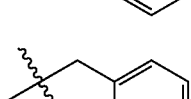 | H |
| 117 | MeO | MeO | —N=CH— | H | 4- | 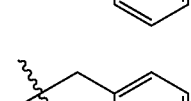 | H |
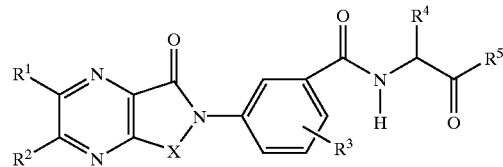
| No. | R¹ | R² | X | R³ | R⁴ | R⁵ |
|---|---|---|---|---|---|---|
| 118 | H | H | —N=CH— | 4-Me | 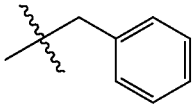 | CONH₂ |
| 119 | H | H | —NHCO— | 4-Me | 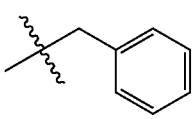 | CONH₂ |

-continued
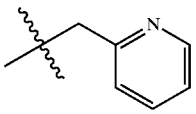
| No. | X | R³ | R⁴ | R⁵ |
|---|---|---|---|---|
| 120 | —CO— | H | 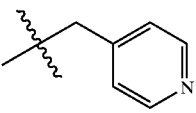 | H |
| 121 | —CO— | H | 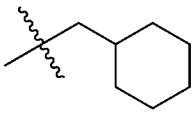 | H |
| 122 | —CO— | H | 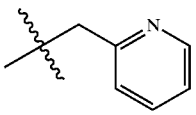 | H |
| 123 | —CO— | 2-NH—COCH₃ | 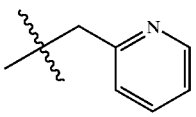 | H |
| 124 | —CO— | H | 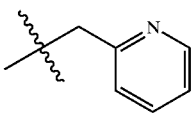 | CONH₂ |
| 125 | —CO— | 4-CH₃ | 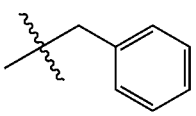 | CONH₂ |
| 126 | —NHCO— | H | 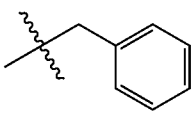 | H |
| 127 | —NHCO— | H | 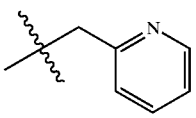 | CONH₂ |
| 128 | —NH—CO— | H | 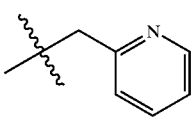 | H |
| 129 | —NH—CO— | H |  | CONH₂ |

-continued

| No. | R¹ | R² | X | R³ | -X¹- | R⁵ |
|---|---|---|---|---|---|---|
| 130 | | | —NH—CO— | 4-CH₃ | (2-pyridylmethyl) | CONH₂ |

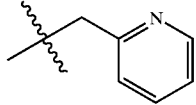

| No. | R¹ | R² | X | R³ | -X¹- | R⁵ |
|---|---|---|---|---|---|---|
| 131 | H | H | —NHCO— | H | 3- | H |
| 132 | Cl | H | —NHCO— | H | 3- | CONH₂ |
| 133 | H | H | —NH—CO— | 4-CH₃ | 3- | CONH₂ |
| 134 | H | H | —NH—CO— | 4-NHCOCH₃ | 3- | H |
| 135 | H | H | —CO— | H | 3- | H |
| 136 | H | H | —CO— | H | 3- | CONH₂ |
| 137 | H | H | —N=CH— | H | 3- | H |
| 138 | Cl | H | —N=CH— | H | 3- | CONH₂ |
| 139 | CH₃O— | CH₃O— | —N=CH— | H | 3- | H |
| 140 | CH₃O— | CH₃O— | —N=CH— | H | 3- | CONH₂ |
| 141 | —(CH₂)₄— | | —CO— | H | 3- | CONH₂ |

We claim:

1. A benzamide of formula I

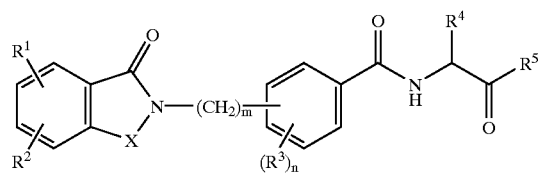

or a tautomeric or isomeric form thereof, or its physiologically tolerated salt,
wherein
$R^1$ is hydrogen, $C_1$–$C_6$-alkyl, O—$C_1$–$C_6$-alkyl, OH, Cl, F, Br, I, $CF_3$, $NO_2$, $NH_2$, CN, COOH, COO—$C_1$–$C_4$-alkyl, —NHCO—$C_1$–$C_4$-alkyl, —NHCO-phenyl, —CONHR$^8$, NHSO$_2$—$C_1$–$C_4$-alkyl, —NHSO$_2$-phenyl, —SO$_2$—$C_1$–$C_4$-alkyl or —SO$_2$-phenyl, $R^2$ is hydrogen, $C_1$–$C_6$-alkyl, O—$C_1$–$C_6$-alkyl, OH, Cl, F, Br, I, $CF_3$, $NO_2$, $NH_2$, CN, COOH, COO—$C_1$–$C_4$-alkyl, —NHCO—$C_1$–$C_4$-alkyl, —NHCO-phenyl, —CONHR$^8$, NHSO$_2$—$C_1$–$C_4$-alkyl, —NHSO$_2$-phenyl, —SO$_2$—$C_1$–$C_4$-alkyl or —SO$_2$-phenyl or $R^1$ and $R^2$ are, together, a chain —CH=CH—CH=CH—, which can additionally carry one or two substituents $R^6$, $R^3$ is hydrogen, chlorine, bromine, fluorine, $C_1$–$C_6$-alkyl, phenyl, NHCO—$C_1$–$C_4$-alkyl, $NO_2$ or $NH_2$, $R^4$ $C_1$–$C_6$-alkyl, which can additionally carry a phenyl, cyclopropyl, cyclobutyl, cyclopentyl, cyclohexyl, cycloheptyl, indolyl, pyridyl or naphthyl ring which, for its part, is substituted by one or two radicals $R^7$, with $R^7$ being hydrogen, $C_1$–$C_4$-alkyl, —O—$C_1$–$C_4$-alkyl, OH, Cl, F, Br, I, $CF_3$, $NO_2$, $NH_2$, CN, COOH, COO—$C_1$–$C_4$-alkyl, —CONHR$^8$, —NHCO—$C_1$–$C_4$-alkyl, —NHCO-phenyl, —NHSO$_2$—$C_1$–$C_4$-alkyl, —NHSO$_2$-phenyl, —SO$_2$—$C_1$–$C_4$-alkyl or —SO$_2$-phenyl, $R^5$ is hydrogen, —CO—OR$^8$, —CO—NR$^9$R$^{10}$,

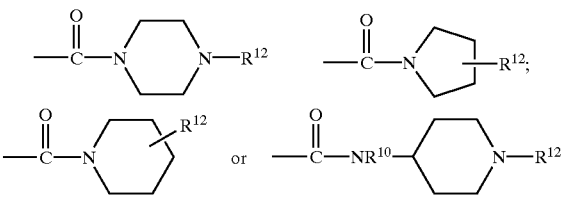

$R^6$ is hydrogen, $C_1$–$C_6$-alkyl, —O—$C_1$–$C_6$-alkyl, OH, Cl, F, Br, I, $CF_3$, $NO_2$, $NH_2$, CN, COOH, COO—$C_1$–$C_4$-alkyl, $R^8$ is hydrogen or $C_1$–$C_6$-alkyl, $R^9$ is hydrogen, $C_1$–$C_6$-alkyl which can additionally be substituted by a phenyl ring which can additionally carry a radical $R^{11}$ and can be substituted by

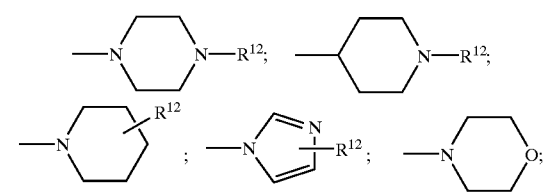

$R^{10}$ is hydrogen or $C_1$-$C_6$-alkyl, $R^{11}$ is hydrogen, $C_1$-$C_6$-alkyl, —O—$C_1$14 $C_6$-alkyl, OH, Cl, F, Br, I, $CF_3$, $NO_2$, $NH_2$, CN, COOH, COO—$C_1$-$C_4$-alkyl, $R^{12}$ is hydrogen or a —$C_{0-4}$-alkyl chain which can be substituted by a phenyl ring which can itself additionally carry one or two radicals $R^{11}$, X is —$CH_2$—$CH_2$—, —CH=CH—, —$SO_2$—, —$CH_2$—, —CO— or —$CH_2$—CO—, n is the number 0, 1 or 2, and m is the number 0, 1 or 2.

2. The benzamide of formula I defined in claim 1, wherein $R^5$ is hydrogen.

3. The benzamide of formula I defined in claim 1, wherein $R^5$ is —CO—$NR^9R^{10}$.

4. The benzamide of formula I defined in claim 1, wherein $R^5$ is —CO—$OR^8$.

5. A pharmaceutical composition comprising an effective amount of the benzamide of formula I defined in claim 1 and a customary carrier or diluent.

6. A drug preparation which comprises an effective amount of the benzamide of formula I defined in claim 1.

7. The composition defined in claim 5, which comprises of from 0.001 to 1% by weight of the benzamide of formula I.

8. The composition defined in claim 5, which comprises of from 0.01 to 0.1% by weight of the benzamide of formula I.

9. The preparation defined in claim 6, which is adapted to be administered as a single dose per day.

10. The preparation defined in claim 9, wherein the effective amount of the benzamide is adapted to correspond to a dose of from 0.1 to 100 mg per kg body weight of a patient to be treated with the preparation.

11. A method for inhibiting cysteine proteases in a patient, which comprises administering to the patient an effective amount of the composition defined in claim 5.

12. A method for treating diseases in a patient in which elevated activities of calpain occur, which comprises administering to the patient an effective amount of the composition defined in claim 5.

13. A method for treating neurodegenerative diseases and neuronal damage in a patient, which comprises administering to the patient an effective amount of the composition defined in claim 5.

14. A method for treating diseases and neuronal damage which are induced by ischemia, trauma or massive hemorrhages in a patient, which comprises administering to the patient an effective amount of the composition defined in claim 5.

15. A method for treating cerebral stroke and cranial/brain trauma in a patient, which comprises administering to the patient an effective amount of the composition defined in claim 5.

16. A method for treating Alzheimer's disease and Huntington's disease in a patient, which comprises administering to the patient an effective amount of the composition defined in claim 5.

17. A method for treating epilepsies in a patient, which comprises administering to the patient an effective amount of the composition defined in claim 5.

18. A method for treating damage to the heart following cardiac ischemias, damage to the kidneys following renal ischemias, skeletal muscle damage, muscular dystrophies, damage which arises due to proliferation of the smooth muscle cells, coronary vasospasm, cerebral vasospasm, cataracts of the eyes and restenosis of the blood vessels following angioplasty which comprises administering to the patient an effective amount of the composition defined in claim 5.

19. A method for treating tumors and their metastases in a patient, which comprises administering to the patient an effective amount of the composition defined in claim 5.

20. A method for treating diseases in which increased levels of interleukin-1 occur in a patient, which comprises administering to the patient an effective amount of the composition defined in claim 5.

21. A method for treating immunological diseases such as inflammations and rheumatic disorders in a patient, which comprises administering to the patient an effective amount of the composition defined in claim 5.

* * * * *

UNITED STATES PATENT AND TRADEMARK OFFICE
CERTIFICATE OF CORRECTION

PATENT NO. : 6,436,949 B1
DATED : August 20, 2002
INVENTOR(S) : Lubisch et al.

It is certified that error appears in the above-identified patent and that said Letters Patent is hereby corrected as shown below:

Column 45,
Line 8, "-O-$C_1$ $14C_6$-alkyl" should be -- -O-$C_1$-$C_6$-alkyl --.

Signed and Sealed this

Fifteenth Day of October, 2002

*Attest:*

*Attesting Officer*

JAMES E. ROGAN
*Director of the United States Patent and Trademark Office*